(12) United States Patent
Hayden et al.

(10) Patent No.: US 12,090,035 B2
(45) Date of Patent: Sep. 17, 2024

(54) ABSORBENT ARTICLE HAVING FASTENING SYSTEM

(71) Applicant: The Procter & Gamble Company, Cincinnati, OH (US)

(72) Inventors: Russell Andrew Hayden, New Richmond, OH (US); Jacob Karun Jayakaran, Greenhills, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 237 days.

(21) Appl. No.: 17/344,997

(22) Filed: Jun. 11, 2021

(65) Prior Publication Data
US 2021/0386601 A1    Dec. 16, 2021

Related U.S. Application Data

(60) Provisional application No. 63/038,292, filed on Jun. 12, 2020.

(51) Int. Cl.
*A61F 13/56* (2006.01)
*A61F 13/62* (2006.01)
*A61F 13/84* (2006.01)

(52) U.S. Cl.
CPC ........ *A61F 13/5644* (2013.01); *A61F 13/622* (2013.01); *A61F 13/84* (2013.01);
(Continued)

(58) Field of Classification Search
CPC .... A61F 13/5644; A61F 13/62; A61F 13/622; A61F 13/84; A61F 2013/5683; A61F 2013/8497; A61F 13/56–82
See application file for complete search history.

(56) References Cited

U.S. PATENT DOCUMENTS 3,848,594 A   11/1974   Buell
3,860,003 A   1/1975    Buell
(Continued)

FOREIGN PATENT DOCUMENTS

CN   204600915 U   9/2015
CN   205053047 U   3/2016
(Continued)

OTHER PUBLICATIONS

All Office Actions; U.S. Appl. No. 17/345,000, filed Jun. 11, 2021.
(Continued)

*Primary Examiner* — Rebecca E Eisenberg
*Assistant Examiner* — Linnae E. Raymond
(74) *Attorney, Agent, or Firm* — Daniel S. Albrecht; Wednesday G. Shipp; Sarah M. DeCristofaro

(57) ABSTRACT

An absorbent article has a first waist region, a second waist region, a crotch region disposed between the first and second waist regions; and a topsheet, a backsheet, and an absorbent core disposed between the topsheet and backsheet. The article also includes a primary fastening system and secondary fastening system. The primary fastening system has a primary fastening component disposed in the second waist region and a primary receiving component disposed in the first waist region and operatively engageable with the primary fastening component. The secondary fastening system includes a secondary fastening component disposed in the first waist region and a secondary receiving component disposed in the second waist region and operatively engageable with the secondary fastening component. The article further includes a graphic at least partially overlapping the secondary fastening component.

18 Claims, 14 Drawing Sheets

(52) U.S. Cl.
CPC ............... *A61F 2013/5683* (2013.01); *A61F 2013/8497* (2013.01)

(56) References Cited

U.S. PATENT DOCUMENTS

| | | | |
|---|---|---|---|
| 3,911,173 A | 10/1975 | Sprague, Jr. | |
| 4,573,986 A | 3/1986 | Minetola | |
| 4,610,678 A | 9/1986 | Weisman | |
| 4,662,875 A | 5/1987 | Hirotsu | |
| 4,673,402 A | 6/1987 | Weisman | |
| 4,785,996 A | 11/1988 | Ziecker | |
| 4,834,735 A | 5/1989 | Alemany | |
| 4,842,666 A | 6/1989 | Werenicz | |
| 4,846,815 A | 7/1989 | Scripps | |
| 4,850,992 A * | 7/1989 | Amaral | A61F 13/533 604/389 |
| 4,888,231 A | 12/1989 | Angstadt | |
| 4,894,060 A | 1/1990 | Nestegard | |
| 4,946,527 A | 8/1990 | Battrell | |
| 5,137,537 A | 8/1992 | Herron | |
| 5,147,345 A | 9/1992 | Lavon | |
| 5,151,092 A | 9/1992 | Buell | |
| 5,156,793 A | 10/1992 | Buell | |
| 5,167,897 A | 12/1992 | Weber | |
| 5,221,274 A | 6/1993 | Buell | |
| 5,242,436 A * | 9/1993 | Weil | A61F 13/49009 604/386 |
| 5,260,345 A | 11/1993 | Desmarais | |
| 5,342,338 A | 8/1994 | Roe | |
| 5,387,207 A | 2/1995 | Dyer | |
| 5,397,316 A | 3/1995 | Young | |
| 5,518,801 A | 5/1996 | Chappell | |
| 5,554,145 A | 9/1996 | Roe | |
| 5,569,234 A | 10/1996 | Buell | |
| 5,580,411 A | 12/1996 | Nease | |
| 5,624,429 A | 4/1997 | Long et al. | |
| 5,628,097 A | 5/1997 | Benson | |
| 5,700,254 A | 12/1997 | Mcdowall | |
| 5,778,457 A | 7/1998 | Conway | |
| 5,993,432 A | 11/1999 | Lodge | |
| 6,004,306 A | 12/1999 | Robles | |
| 6,061,881 A | 5/2000 | Takizawa et al. | |
| 6,120,487 A | 9/2000 | Ashton | |
| 6,174,303 B1 | 1/2001 | Suprise et al. | |
| 6,410,129 B2 | 6/2002 | Zhang | |
| 6,432,098 B1 | 8/2002 | Kline | |
| 6,468,257 B1 | 10/2002 | Ono et al. | |
| 6,478,784 B1 | 11/2002 | Johnson et al. | |
| 6,613,032 B2 | 9/2003 | Ronnberg et al. | |
| 6,616,649 B1 | 9/2003 | Ismail | |
| 6,677,258 B2 | 1/2004 | Carroll | |
| 6,746,434 B2 | 6/2004 | Johnson et al. | |
| 6,764,475 B1 | 7/2004 | Olson | |
| 6,843,134 B2 | 1/2005 | Anderson | |
| 6,878,647 B1 | 4/2005 | Rezai | |
| 6,884,494 B1 | 4/2005 | Curro | |
| 6,890,872 B2 | 5/2005 | Bond | |
| 6,905,987 B2 | 6/2005 | Noda | |
| 6,926,705 B1 | 8/2005 | Coates | |
| 6,964,720 B2 | 11/2005 | Schneider | |
| 7,060,149 B2 | 6/2006 | Ortega | |
| 7,062,983 B2 | 6/2006 | Anderson | |
| 7,211,531 B2 | 5/2007 | Schneider | |
| 7,223,818 B2 | 5/2007 | Autran | |
| 7,254,874 B2 * | 8/2007 | Duffy | A44B 18/0049 24/452 |
| 7,264,615 B2 | 9/2007 | Sherrod et al. | |
| 7,435,243 B2 | 10/2008 | Miyamoto | |
| 7,806,883 B2 | 10/2010 | Fossum | |
| 7,819,853 B2 | 10/2010 | Desai | |
| 8,062,279 B2 | 11/2011 | Miyamoto | |
| 8,435,223 B2 | 5/2013 | Roe | |
| 8,496,640 B2 | 7/2013 | Molander | |
| 8,546,641 B2 | 10/2013 | Roe | |
| 8,618,350 B2 | 12/2013 | Mansfield | |
| 8,636,710 B2 | 1/2014 | Ellingson et al. | |
| 8,759,605 B2 | 6/2014 | Roe | |
| 8,784,722 B2 | 7/2014 | Rocha | |
| 8,795,809 B2 | 8/2014 | Mansfield | |
| 8,808,263 B2 | 8/2014 | Roe | |
| 8,834,442 B2 | 9/2014 | Miyake et al. | |
| 8,932,273 B2 | 1/2015 | Roe | |
| 8,939,957 B2 | 1/2015 | Raycheck | |
| 8,998,870 B2 | 4/2015 | Roe | |
| 9,011,398 B2 | 4/2015 | Johnston et al. | |
| 9,011,402 B2 | 4/2015 | Roe | |
| 9,078,789 B2 | 7/2015 | Wang | |
| 9,089,456 B2 | 7/2015 | Roe | |
| 9,339,425 B2 * | 5/2016 | Stabelfeldt | A61F 13/55115 |
| 9,387,138 B2 | 7/2016 | Roe | |
| 9,597,237 B2 | 3/2017 | Enz | |
| 9,795,194 B2 | 10/2017 | Rocha | |
| 9,849,043 B2 | 12/2017 | Barnes et al. | |
| 10,076,162 B2 | 9/2018 | Rocha | |
| 10,798,997 B2 | 10/2020 | Rocha | |
| 11,426,312 B2 * | 8/2022 | Collins | A61F 13/15747 |
| 2002/0151858 A1 | 10/2002 | Karami | |
| 2002/0169435 A1 | 11/2002 | Neeb | |
| 2003/0119404 A1 | 6/2003 | Belau | |
| 2005/0079321 A1 | 4/2005 | Tuman et al. | |
| 2005/0164587 A1 | 7/2005 | Melik | |
| 2006/0167432 A1 | 7/2006 | Sigari | |
| 2006/0293639 A1 * | 12/2006 | Van Gompel | A61F 13/62 604/385.01 |
| 2007/0203301 A1 | 8/2007 | Autran | |
| 2007/0219521 A1 | 9/2007 | Hird | |
| 2007/0249254 A1 | 10/2007 | Mansfield | |
| 2007/0287348 A1 | 12/2007 | Autran | |
| 2007/0287983 A1 | 12/2007 | Lodge | |
| 2007/0293111 A1 | 12/2007 | Mansfield | |
| 2008/0045917 A1 | 2/2008 | Autran | |
| 2008/0319407 A1 | 12/2008 | Trinkaus | |
| 2009/0258210 A1 | 10/2009 | Iyad | |
| 2010/0180407 A1 | 7/2010 | Rocha | |
| 2011/0139657 A1 | 6/2011 | Hird | |
| 2011/0139658 A1 | 6/2011 | Hird | |
| 2011/0139659 A1 | 6/2011 | Hird | |
| 2011/0144609 A1 | 6/2011 | Petersen et al. | |
| 2011/0152812 A1 | 6/2011 | Hird | |
| 2012/0022485 A1 | 1/2012 | Roe et al. | |
| 2012/0022491 A1 | 1/2012 | Roe | |
| 2013/0006209 A1 | 1/2013 | Ruiz | |
| 2013/0082418 A1 | 4/2013 | Curro | |
| 2013/0324959 A1 | 12/2013 | Ashraf et al. | |
| 2014/0000003 A1 | 1/2014 | Ashraf et al. | |
| 2014/0005621 A1 | 1/2014 | Roe | |
| 2014/0012220 A1 | 1/2014 | Flieg | |
| 2014/0257226 A1 | 9/2014 | Wang et al. | |
| 2016/0136014 A1 | 5/2016 | Arora | |
| 2017/0027775 A1 | 2/2017 | Barnes et al. | |
| 2017/0181905 A1 | 6/2017 | Sakurai et al. | |
| 2018/0042777 A1 | 2/2018 | Dalal | |
| 2018/0042778 A1 | 2/2018 | Lenser | |
| 2018/0050484 A1 | 2/2018 | Rocha | |
| 2018/0228664 A1 | 8/2018 | Hou | |
| 2018/0271716 A1 | 9/2018 | Dalal | |
| 2018/0271717 A1 | 9/2018 | Dria | |
| 2019/0209400 A1 | 7/2019 | Collins et al. | |
| 2020/0179184 A1 | 6/2020 | Kaiser | |
| 2021/0007912 A1 | 1/2021 | Swedberg et al. | |
| 2021/0251818 A1 | 8/2021 | Roe et al. | |
| 2021/0251824 A1 | 8/2021 | Roe | |
| 2021/0251825 A1 | 8/2021 | Roe | |

FOREIGN PATENT DOCUMENTS

| | | |
|---|---|---|
| EP | 0446818 A2 | 9/1991 |
| EP | 3481355 B1 | 8/2020 |
| JP | 2011156309 A | 8/2011 |
| JP | 2012050575 A | 3/2012 |
| WO | 9510996 A1 | 4/1995 |
| WO | 0015069 A1 | 3/2000 |
| WO | 0059430 A1 | 10/2000 |
| WO | 03003960 A2 | 1/2003 |

(56) References Cited

FOREIGN PATENT DOCUMENTS

| WO | 02067809 A3 | 4/2003 |
|----|-------------|--------|
| WO | 2011129097 A1 | 10/2011 |
| WO | 2013147059 A1 | 10/2013 |
| WO | 2014073637 A1 | 5/2014 |
| WO | 2015167533 A2 | 11/2015 |
| WO | 2016085960 A1 | 6/2016 |
| WO | 2019043640 A1 | 3/2019 |
| WO | 2019120574 A1 | 6/2019 |
| WO | 2019155403 A1 | 8/2019 |
| WO | 2020041271 A1 | 2/2020 |

OTHER PUBLICATIONS

Unpublished U.S. Appl. No. 17/345,000, filed Jun. 11, 2021, to first inventor Jeromy Thomas Raycheck et al.
PCT Search Report and Written Opinion for PCT/US2021/036902 dated Oct. 11, 2021, 12 pages.
All Office Actions; U.S. Appl. No. 17/173,471, filed Feb. 11, 2021.

\* cited by examiner

ABSORBENT ARTICLE HAVING FASTENING SYSTEM

CROSS REFERENCE TO RELATED APPLICATION

This application claims the benefit of U.S. Provisional Application No. 63/038,292, filed Jun. 12, 2020, the substances of which are incorporated herein by reference.

FIELD OF THE INVENTION

The present disclosure relates to absorbent articles having fastening systems, in particular articles having multiple fastening systems.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer. Fastening systems have been used to ensure the article is secured about the wearer and remains in place. One popular configuration of absorbent article/fastening system includes an absorbent chassis having a front waist region, crotch region and rear waist region, with a pair of fastening members each extending respectively laterally from left and right longitudinal edges of the chassis in the rear waist region. In a typical configuration, each fastening member includes a patch of material bearing hooks, affixed to the wearer-facing side of the fastening member. A section of cooperating loops material is typically disposed on the garment-facing side of the front waist region. In this configuration, the chassis may be wrapped through the wearer's crotch area with the back waist region placed across the wearer's lower back and buttocks and the front waist region placed across the wearer's lower belly area. The left and right fastening members may then be wrapped about the wearer's left and right hips, respectively, and fastened to the front waist region via engagement of the hooks with the loops material on the front waist region, thereby securing the diaper on the wearer.

To further ensure fit and prolonged attachment about the waist, a secondary fastening system may be included, which may include hooks affixed to the garment-facing side of the front waist region and cooperating hook receiving material (e.g., loops) on the wearer-facing side of the back waist region. Because the secondary fastening system provides additional areas of attachment and anchoring, the front and back waist regions may better conform to the wearer, reducing gaps and sagging both at application and during use. The secondary fastening system also reduces potential rotation of the waist regions and/or flipping of material at the waist that often occurs when exudates weigh down the crotch region of the article.

The secondary fastening component may not be visible or apparent to the user. Therefore, there is a need to provide a mechanism for better instructing users on the location and use of the secondary fastening system.

SUMMARY OF THE INVENTION

The invention comprises the features of the independent claims herein. An absorbent article comprises a first waist region, a second waist region, a crotch region disposed between the first and second waist regions; and a topsheet, a backsheet, and an absorbent core disposed between the topsheet and backsheet. The absorbent article comprises a primary fastening system and secondary fastening system, wherein the primary fastening system comprises a primary fastening component disposed in the second waist region and a primary receiving component disposed in the first waist region and operatively engageable with the primary fastening component. The secondary fastening system comprises a secondary fastening component disposed in the first waist region and a secondary receiving component disposed in the second waist region and operatively engageable with the secondary fastening component. The article comprises a fastening area graphic disposed in the first waist region in at least partial overlapping relationship with the secondary fastening component; wherein the secondary fastening component comprises a first periphery having a first shape and a fastening component area, and the graphic comprises a second shape and a graphic area. The first and second shapes are different.

An absorbent article comprises a first waist region, a second waist region, a crotch region disposed between the first and second waist regions; and a topsheet, a backsheet, and an absorbent core disposed between the topsheet and backsheet. The article comprises a primary fastening system and secondary fastening system, wherein the primary fastening system comprises a primary fastening component disposed in the second waist region and a primary receiving component disposed in the first waist region and operatively engageable with the primary fastening component. The secondary fastening system comprises a secondary fastening component disposed in the first waist region and a secondary receiving component disposed in the second waist region and operatively engageable with the secondary fastening component. The article comprises a graphic disposed in the first waist region in at least partial overlapping relationship with the secondary fastening component, such that a first portion of the graphic overlaps the secondary fastening component and a second portion of the graphic does not overlap the secondary fastening component; and the first portion differs from the second portion by one of the following: color, color intensity, transparency, reflection, saturation, two-dimensional area, shape, print resolution and combinations thereof.

A method of forming a fastening component comprising the steps of:
  providing a substrate having a colored portion having a first portion and a second portion;
  providing a first plurality of fastening elements; and
  overlapping the first plurality of fastening elements with the first portion but not the second portion, such that the second portion is void of the first plurality of fastening elements.

DETAILED DESCRIPTION OF THE INVENTION

Definitions

Figure 1:
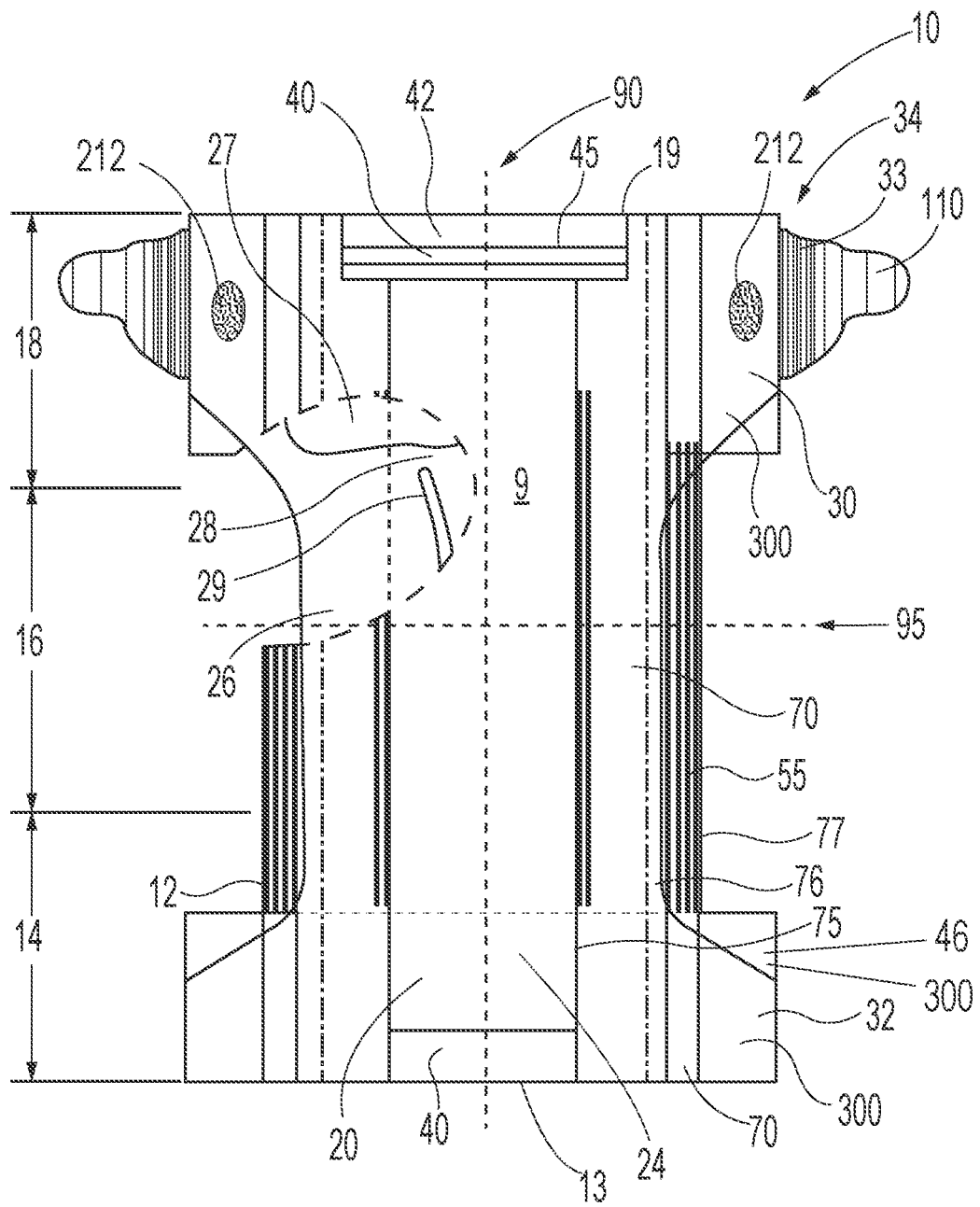
FIG. 1 is a schematic plan view of an exemplary absorbent article according to one nonlimiting embodiment of the present invention. The absorbent article is shown in a flat, uncontracted state.

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Disposable," in reference to articles, means that the articles are generally not intended to be laundered or otherwise restored or reused in the same capacity (i.e., they are intended to be discarded after a single use and, preferably, to be recycled, composted or otherwise discarded in an environmentally compatible manner).

"Disposed" refers to an element being located in a particular place or position. A feature that is disposed on a surface or side of a component may be integral with said component or may be joined to said component.

"Elastic" and "elastomeric" mean the ability of a material to stretch by at least 50% without rupture or breakage at a given load, and upon release of the load the elastic material or component exhibits at least 70% recovery (i.e., has less than 30% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below.

"Extensible" means the ability to stretch or elongate, without rupture or breakage, by at least 50% as per step 6(a) in the Hysteresis Test herein.

"Inboard," with respect to a first feature of an article and its position relative a second feature or location on the article, means that the first feature lies closer to a respective axis of the article than the second feature or location, along a horizontal x-y plane approximately occupied by the article when laid out flat, extended to the full longitudinal and lateral dimensions of its component web materials against any contraction induced by any included pre-strained elastomeric material, on a horizontal surface. Laterally inboard means the first feature is closer to the longitudinal axis, and longitudinally inboard means the first feature is closer to the lateral axis. Conversely, "outboard," with respect to a first feature of an article and its position relative a second feature or location on the article, means that the first feature lies farther from the respective axis of the article than the second feature or location.

"Integral" means configurations whereby an element is created from or created by an article component, or portions thereof, as opposed to being joined to the component. "Integrally formed" means an element is created from an underlying material or portion thereof, by for example molding, shaping and/or reconstituting the material.

"Joined" means configurations whereby an element is directly secured to another element by affixing the element directly to the other element, and configurations whereby an element is indirectly secured to another element by affixing the element to intermediate member(s) that in turn are affixed to the other element.

"Longitudinal" means a direction lengthwise running parallel to the maximum linear dimension in the x-y plane of the absorbent article. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article. Longitudinal dimensions of article components are determined based on the component's configuration on the final absorbent article.

"Lateral" refers to a direction generally perpendicular to the longitudinal direction. In the absorbent article described herein, the lateral direction runs substantially parallel from a side edge to an opposing side edge.

"Visible" means capable of being seen by the human eye having 20/20 vision from at least 12 inches away along a line perpendicular to the x-y plane of the article.

Overview

Figure 2:
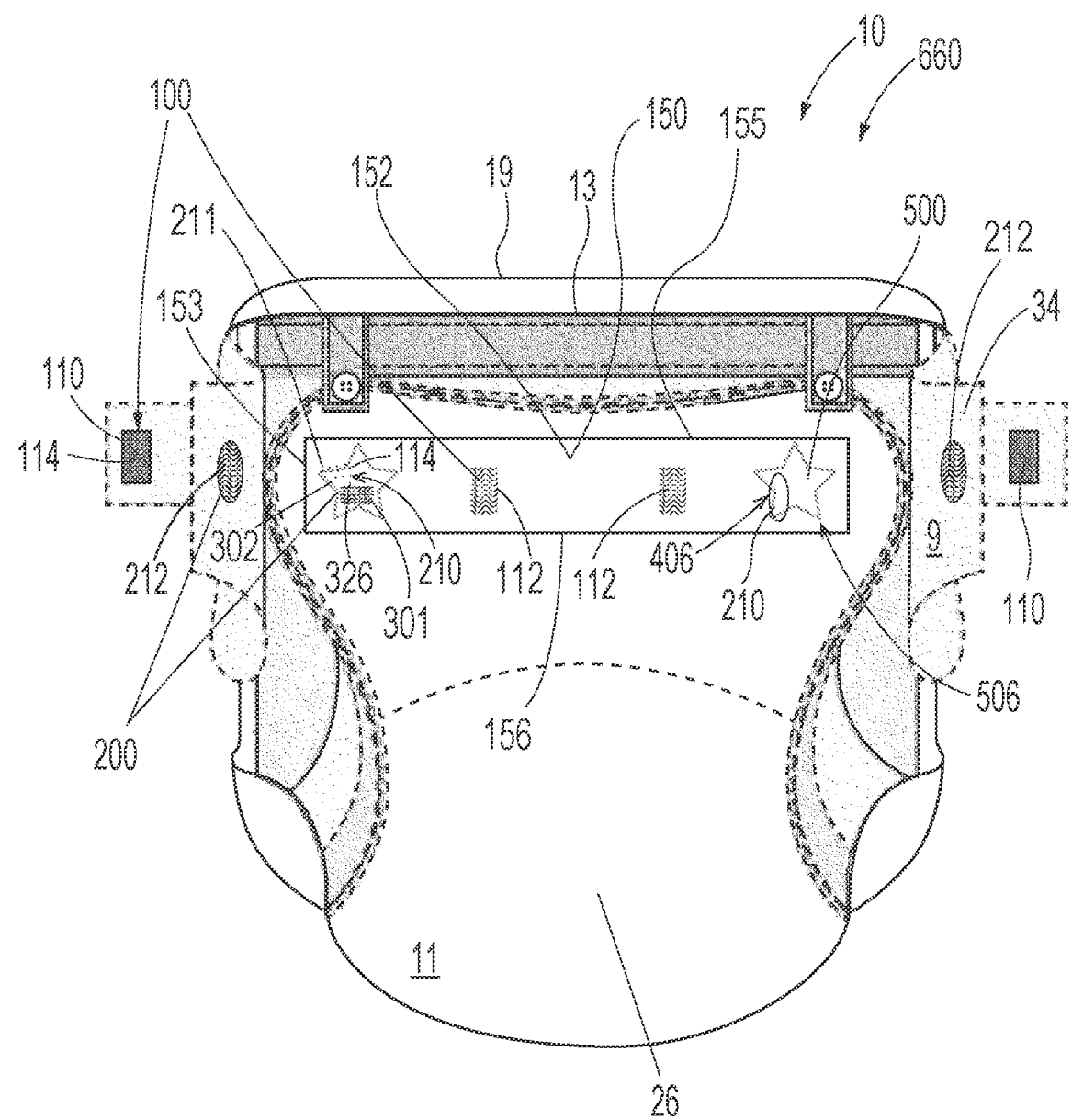
FIG. 2 is a schematic plan view of an exemplary absorbent article according to a nonlimiting embodiment. The absorbent article is shown in a folded state.

FIG. 1 is a plan view of an exemplary, nonlimiting embodiment of an absorbent article 10 of the present invention in a flat, uncontracted state in an unfolded configuration 650. The article may be disposable. The body-facing surface 9 of the absorbent article 10 is facing the viewer. The absorbent article 10 comprises a chassis 20. The absorbent article 10 and chassis 20 are shown to have a first waist region 14, a second waist region 18 opposed to the first waist region 14, and a crotch region 16 located between the first waist region 14 and the second waist region 18. The waist regions 14 and 18 generally comprise those portions of the absorbent article which, when worn, encircle the waist of the wearer. FIG. 2 illustrates an exemplary absorbent article in a folded configuration 660. As shown in FIG. 2, the article may comprise a primary fastening system 100 and a secondary fastening system 200 in the waist regions. The fastening systems and surrounding areas are configured to distribute forces and mitigate the effects of tension during wear better than known articles. A fastening system comprises a fastening component (e.g., fastening component 210). The fastening component is at least in partial overlapping relationship with a graphic 500. The graphic may comprise a shape that differs from the shape of the fastening component. Additionally, or alternatively, the graphic may appear differently in the area of overlap than it appears in the nonoverlapping area (e.g., segments of the graphic may differ by color intensity, transparency, saturation, size, shape, print resolution and combinations thereof).

The fastening component comprises a periphery, which may have a maximum longitudinal dimension disposed outboard of the periphery's inboard-most extent. Additionally, or alternatively, the inboard-most extent of the fastening component (in particular the second fastening component) may be disposed laterally inboard of an article longitudinal foldline. These and other features are described in more detail below.

Absorbent Article

Returning to FIG. 1, the absorbent article 10 includes a longitudinal centerline 90 and a lateral centerline 95. The outer periphery of the chassis 20 is defined by longitudinal edges 12 and waist edges (first waist edge 13 in first waist region 14 and second waist edge 19 in second waist region 18). The chassis 20 may have opposing longitudinal edges 12 that are oriented generally parallel to the longitudinal centerline 90. However, for better fit, longitudinal edges 12 may be curved or angled to produce, for example, an "hourglass" shape article when viewed in a plan view as shown in FIG. 1. The chassis 20 may have opposing lateral edges 13, 19 (i.e., the first waist edge 13 and second waist edge 19) that are oriented generally parallel to the lateral centerline 95.

The chassis 20 may comprise a liquid permeable topsheet 24, a backsheet 26, and an absorbent core 28 between the topsheet 24 and the backsheet 26. The absorbent core may comprise absorbent material, including for example superabsorbent particles and absorbent gelling materials (AGM). The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 27 is disposed between the topsheet 24 and the absorbent core 28.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306. One or more masking layers or materials may be provided in the absorbent article. A masking layer may be a layer that provides a cushiony feel when the absorbent article is touched from the garment-facing surface or the wearer-facing surface. The masking layer may "mask" a grainy feel potentially caused by the absorbent material, such as superabsorbent polymers. The masking layer may "mask" bodily exudates from being visible when viewing the wearer-facing surface or the garment-facing surface of the absorbent article. The masking layer may have a basis weight in the range of about 15 gsm to about 50 gsm or about 15 gsm to about 40 gsm. The masking layer may comprise one or more nonwoven materials (e.g., a hydroentangled nonwoven material), foams, pulp layers, and/or other suitable materials. The masking layer may be the outer cover material of the backsheet. The masking layer may be the layer forming the garment-facing side or the wearer-facing side of the core. The masking layer may be a separate material positioned intermediate the garment-facing side of the core and the liquid impermeable backsheet.

Components of the disposable absorbent article can at least partially be comprised of bio-sourced content as described in U.S. Pat. Pub. Nos. 2007/0219521A1, 2011/0139658A1, 2011/0139657A1, 2011/0152812A1, and 2011/0139659A1. These components include, but are not limited to, topsheets, backsheet films, backsheet nonwovens, side panels, leg gasketing systems, superabsorbent, acquisition layers, core wrap materials, adhesives, fastener systems, and landing zones. In at least one embodiment, a disposable absorbent article component comprises a bio-based content value from about 10% to about 100%, or from about 25% to about 75%, or from about 50% to about 60% using ASTM D6866-10, method B. In order to apply the methodology of ASTM D6866-10 to determine the bio-based content of any component, a representative sample of the component must be obtained for testing. In at least one embodiment, the disposable absorbent article component can be ground into particulates less than about 20 mesh using known grinding methods (e.g., WILEY® mill), and a representative sample of suitable mass taken from the randomly mixed particles.

Topsheet

The topsheet 24 is generally a portion of the absorbent article 10 that may be positioned at least in partial contact or close proximity to a wearer. Suitable topsheets 24 are generally supple, soft feeling, and non-irritating to a wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Absorbent Core

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials (AGM); or any other known absorbent material or combinations of materials. In certain embodiments, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80%, or greater than about 85%, or greater than about 90%, or greater than about 95% by weight of the core. In some embodiments, the absorbent core may comprise one or more channels 29, wherein said channels are substantially free of absorbent particulate polymer material. The channels 29 may extend longitudinally or laterally. The absorbent core may further comprise two or more channels. The channels may be straight, curvilinear, angled or any workable combination thereof. In nonlimiting examples, two channels are symmetrically disposed about the longitudinal axis. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316, and U.S. patent application Ser. Nos. 13/491,642 and 15/232,901.

Backsheet

The backsheet 26 is generally positioned such that it may be at least a portion of the garment-facing surface 11 of the absorbent article 10 as shown in FIG. 2. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. The backsheet may, for example, be or comprise a thin plastic film, such as a thermoplastic film having a thickness of about 0.012 mm to about 0.051 mm. Other suitable backsheet 26 materials may include breathable materials that permit vapors to escape from the absorbent article 10 while still preventing exudates from passing through the backsheet 26.

Backsheet 26 may also consist of more than one layer. The backsheet 26 may comprise an outer cover and an inner layer. The outer cover may be made of a soft, nonwoven material. The inner layer may be made of a substantially liquid-impermeable film, such as a polymeric film. The outer cover and an inner layer may be joined together by adhesive or any other suitable material or method. The outer cover material may comprise a bond pattern, apertures, and/or three-dimensional features. The outer cover may be a hydroentangled nonwoven material.

Extension Elements and Waist Features

The absorbent article 10 may include one or more lateral extension elements 300 (i.e., an element that extends laterally outboard of the longitudinal edge 12 of the chassis). The lateral extension element 300 may be disposed in a waist region. Nonlimiting examples of lateral extension elements include ears 30, belts (which also cover a longitudinally central portion of a waist region), fastener attachment arms 33 (see FIG. 1) and workable combinations thereof.

In certain embodiments, the article 10 includes one or more lateral extension elements in the form of an ear 30, including for example front ears 32 disposed in the first waist region and/or back ears 34 disposed in the second waist region. An ear 30 may be integral with the chassis or a discrete element joined to the chassis 20. An ear 30 may be extensible or elastic. An ear 30 may be formed from one or more nonwoven webs, woven webs, knitted fabrics, polymeric and elastomeric films, apertured films, sponges, foams, scrims or combinations and/or laminates of any the foregoing.

In some embodiments, an ear 30 may include elastomers, such that the ear is stretchable. In certain embodiments, an ear 30 may be formed of a stretch laminate such as a nonwoven/elastomeric material laminate or a nonwoven/elastomeric material/nonwoven laminate, which also results in the ear being stretchable. The ear 30 may be extensible in the lateral direction of the article. In some embodiments, the ear is elastic in the lateral direction. In further embodiments, the ear 30 may extend more in the lateral direction than in the longitudinal direction. Alternatively, the ear may extend more in the longitudinal direction than in the lateral direction. In certain nonlimiting examples, the ear may include one or more inelastic regions along with a separate elastic region. In some embodiments, the area of the elastic region comprises at least about 20%, or from about 30% to about 80%, of the total area of the ear, reciting for said range every 5% increment therein. An inelastic region may be disposed laterally outboard of an elastic region. In nonlimiting examples, an elastic region is disposed between two inelastic regions.

Any suitable nonwoven may be used in an ear 30. Suitable nonwovens may comprise a basis weight of at least about 8 gsm, or less than about 22 gsm, or about 17 gsm or less, or from about 10 gsm to about 20 gsm, reciting for said range every 1 increment therein. Where the ear 30 comprises more than one nonwoven, the nonwovens may comprise the same basis weight or different basis weights. Likewise, the nonwovens may comprise the same layer structure or different layer structures. Further, a nonwoven in the ear may comprise the same or different features of nonwovens in the backsheet, topsheet, leg gasketing system and/or waist feature.

Nonlimiting examples of suitable elastomeric materials include film (e.g., polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, scrims, strands and the like. Elastomeric materials can be formed from elastomeric polymers including polymers comprising styrene derivatives, polyesters, polyurethanes, polyether amides, polyolefins, combinations thereof or any suitable known elastomers including but not limited to co-extruded VISTAMAXX®.

The ear may be activated by processes disclosed in U.S. Pat. Pub. No. 2013/0082418, U.S. Pat. Nos. 5,167,897; 5,993,432; 5,156,793; 5,167,897; 7,062,983 and 6,843,134 for example. Alternatively, the ear 30 comprises a gathered laminate, wherein one of the layers is strained to a greater degree than a remaining layer during lamination and/or bonding. In this way, the less extensible layer (i.e., a nonwoven) will form gathers when the laminate is in a relaxed state. Corrugations then form in the nonwoven layer(s) when the subsequently formed laminate is in a relaxed state. The ear may comprise an ultrasonically bonded laminate as is disclosed for example in U.S. Pat. Pub. Nos. 2018/0042777, 2018/0042778; 2018/0271716; and 2018/0271717.

Where an article 10 comprises multiple ears 30, said ears 30 may be the same or may be different. By way of nonlimiting example, a back ear 34 may comprise an elastic ear while a front ear 32 may be inelastic. Additionally, or alternatively, layers of a front ear may be joined by different means than layers of a back ear. For example, the front ear layers may be joined by adhesive, and back ear layers may be joined by ultrasonic bonds.

The absorbent article 10 may comprise a waist feature 40. Waist features 40 may be disposed in the first waist region 14 and/or in the second waist region 18. In some nonlimiting examples, one or both of the article's waist edges 13, 19 may be at least partially defined by a waist feature as illustrated in FIG. 1. In further nonlimiting examples, a waist feature may be disposed inboard of the closest waist edge. A waist feature may be integral with one or more layers of the chassis, cuffs and/or other elements in the waist region, or may be discrete and joined to one or more layers of the chassis, leg cuff structures and/or other elements disposed in the waist region. The waist feature may be joined between layers, on the outward-facing surface 11 of the article, or on the wearer-facing surface 9 of the article. The waist feature may be extensible or elastic. An elasticized waist feature 42 is generally intended to expand and contract to dynamically fit the wearer's waist. Elasticized waist features include waistbands, waist cuffs having pockets formed from a portion of the waist feature that is unattached from the chassis 20, and waist panels and/or belts designed to fit securely about the abdomen of the wearer in diaper, pants or other article configurations. Nonlimiting examples of elasticized waist features are disclosed in U.S. patent application Ser. Nos. 14/533,472; 15/074,675 and 62/855,001. Elasticized waist features may comprise one or more nonwoven layers and one or more elastic elements 45. In nonlimiting examples, the elasticized waist feature comprises elastic strands joined to the nonwoven layer(s). In further nonlimiting examples, the elasticized waist feature comprises a laminate of one or more nonwoven layers and one or more films.

In alternative embodiments, the waist feature may be inelastic. In such configurations, the waist feature may provide additional anchoring about the waist of the wearer.

A waist feature can be used in conjunction with an ear 30 to provide desirable stretch and flexibility, or otherwise enhance fit of the article on the wearer.

In some embodiments, a lateral extension element may be in the form of a belt such that it also constitutes a waist feature. The lateral extension element 300 may comprise a combination belt structure 46, formed from a web material 47, which extends through the waist region and laterally outboard of the longitudinal edges of the chassis as shown in waist region 14 in FIG. 1. By combination belt structure 46, it is meant that the element is configured to both (i) provide and/or support a receiving component of a fastening system (discussed below) and (ii) form one or more ears 30 that extend outboard of a longitudinal edge 12 of the chassis. In the nonlimiting examples, the combination belt structure 46 is configured to provide and/or support primary receiving components 112 as well as secondary fastening components 210, each of which is discussed below.

Fasteners

Returning to FIG. 2, the absorbent article 10 includes one or more fastening systems 100. In the embodiment shown in FIG. 2, the article comprises a primary fastening system 100 and a secondary fastening system 200. When fastened, the primary fastening system 100 interconnects the first waist region 14 and the rear waist region 18 resulting in a waist circumference that may encircle the wearer during wear of the absorbent article 10. Likewise, when fastened the secondary fastening system 200 interconnects the waist regions.

One or more portions of the fastening system may be formed from, or may be joined to, a lateral extension element 300. Additionally, or alternatively, portions of the fastening system may be formed from, or may be joined to, the chassis 20. In embodiments where the portions of the fastening system are joined, said portions may be joined to an exterior surface or between layers. In embodiments where portions of the fastening system are integral, said portions may be integral with any suitable surface.

Each fastening system may comprise a fastening component and a receiving component. The receiving component is operatively engageable with the fastening component. Nonlimiting examples of engageable fastening and receiving components include tape tabs, hook and loop fastening components, interlocking fasteners such as tabs & slots, buckles, buttons, snaps, and/or hermaphroditic fastening components. Some exemplary surface fastening systems are disclosed in U.S. Pat. Nos. 3,848,594; 4,662,875; 4,846,815; 4,894,060; 4,946,527; 5,151,092; and 5,221,274. A fastening component and/or receiving component may further include a release tape or other material that protects the component from insult prior to use. In nonlimiting examples, the fastening component and/or the component to which it is joined is foldable and may be folded prior to use such that the fastening component engages with material that protects it from insult. While shown in the waist region, it is also contemplated that a fastening and/or a receiving component may be disposed in any portion of the diaper, which may facilitate closing or wrapping the article during disposal, securing the article to itself and/or securing the article to another surface such as a garment.

A fastening component 110 comprises one or more fastening elements 114 which cause the component to engage with another surface, such as the receiving component. In various embodiments, fastening elements comprise hooks. Receiving component 112 comprises material adapted to fastenably cooperate with fastening elements, such as a section or patch adapted to serve as cooperative loops material, to provide a hook-and-loop fastening system combination. The fastening and/or receiving components may be discrete from and joined to article components 150 or may be integral with one or more article components 150. Article components 150 may be selected from the chassis 20, topsheet 24, backsheet 26, a lateral extension element 300, an ear 30, a landing zone 152 (i.e., a substrate or portion of the chassis comprising a receiving component), a fastener attachment arm 33, a waist feature 40, a combination belt structure 46 or combinations thereof. In nonlimiting examples, material forming a portion of an article component may comprise integral loops material. In further nonlimiting examples, fastening components and receiving components may be formed on the same patch of material.

In certain embodiments, a fastening component may be longitudinally offset from a lateral edge of the article component on which the fastening component is disposed. The fastening component may be longitudinally offset from an outboard lateral edge 155 of the component by at least 1 mm, or at least about 3 mm, or at least about 5 mm, or from about 1 mm to about 10 mm, reciting for said range every 0.5 mm increment therein. In nonlimiting examples, a fastening component does not coincide with either the inboard edge 156 or outboard edge 155 of the component on which it is disposed. It may be desired, for example, that each secondary fastening component 210 (discussed further below) is disposed with its surface area and outer edges entirely within the surface area and outer edges of the lateral extension element, or other article component, on which it is disposed. Additionally, or alternatively, a fastening component may be laterally offset from a longitudinal edge of a component on which it is disposed. For instance, an outboard edge 211 of a secondary fastening component 210 may be laterally inboard of a longitudinal edge 153 by at least about 1 mm, or at least about 3 mm, or at least about 5 mm, or from about 1 mm to about 10 mm, reciting for said range every 0.5 mm increment therein. In nonlimiting examples, the outboard edge 211 of the secondary fastening component may be laterally inboard of a chassis edge 12.

Still referring to FIG. 2, the primary fastening system 100 comprises a primary fastening component 110, such as hooks, disposed in the second waist region 18. The primary fastening component 110 may be discrete, such as a discrete patch of fastening material joined to the chassis or joined to another component in the second waist region. In nonlimiting examples, the primary fastening component is joined to an ear 34 or a separate layer joined to the ear. In another nonlimiting example, the primary fastening component may be integral with an ear. In further nonlimiting examples, the primary fastening component 110 may be integral with the chassis and/or another component joined to the chassis.

In some embodiments, the primary fastening component 110 may be separately applied sections or patches of hooks material that are bonded to a back ear or chassis by heat, compression, adhesive, ultrasonic bonding or any combination thereof. In other examples, a primary fastening component may be a patch of hooks that are formed directly on a section of the ear, more particularly formed directly on a section of a polymeric layer of nonwoven. For example, the hooks may be produced via application of molten polymer resin onto the layer, and subsequent formation of hooks in and from the melted, applied resin via known methods. The primary fastening components may be integrally formed from polymeric material by heating and softening a portion of the material and pressing it into hook-forming cavities, as is disclosed in U.S. Pat. No. 8,784,722. The primary fastening components may be integrally formed from the polymeric material through a single continuous process as is disclosed in commonly assigned U.S. patent application Ser. No. 16/545,425.

Still referring to FIG. 2, the primary fastening system 100 may further comprise a primary receiving component 112, such as loops, disposed in the first waist region 14. The primary receiving component may be discrete, such as a discrete patch of receiving material joined to the chassis or joined to another component in the first waist region. In other embodiments, the primary receiving component may be integral with the chassis or integral with another component in the first waist region. In such embodiments, the backsheet 26, a combination belt structure 46, an ear 30 or combinations thereof may comprise material, such as loop material, which may form the primary receiving component 112.

The primary components 110, 112 may each be any suitable shape or size. The primary components 110, 112 may be disposed on opposite surfaces of the article. For instance, the primary fastening component 110 may be disposed on the wearer-facing surface 9 of the article and the primary receiving component may be disposed on the garment-facing surface 11.

In various embodiments, the article also comprises a secondary fastening system 200. The secondary fastening system 200 comprises a secondary fastening component 210 and a secondary receiving component 212 that are operatively engageable to further secure the article about the wearer. The secondary fastening component 210 may be disposed in the first waist region, and the secondary fastening receiving component 212 may be disposed in the second waist region. Addition of a secondary fastening system can provide a greater surface area for fastening, and thereby de-concentrate lateral tensile forces communicated through the fastening location(s) as the rear waist region is pulled toward the front waist region, and vice versa, when the diaper is worn. In addition, having two distinct fastening locations reduces the tendency of the front portion of the article to pivot (i.e., pivot around the single fastening location of the primary fastening system). Further, the secondary system helps to create a line of tension closer to the front waist edge, which may reduce the likelihood of folding or flipping over of the front waist edge during wear. Further still, the secondary system may create an anchoring geodesic to direct forces from the crotch region to over the hips in order to prevent sagging during wearer. The secondary system may also help to secure the front ear or combination belt structures in place during wear. Each of the foregoing can serve to provide for more effective and durable fastening and less longitudinal and/or lateral flexing, sagging and/or wrinkling of the diaper materials about the fastening areas during wear.

The secondary components 210, 212 may be disposed on opposite surfaces (e.g., the secondary fastening component may be disposed on the garment-facing surface 11 and the secondary receiving component may be disposed on the wearer-facing surface 9). The secondary fastening system may comprise any of the features detailed above with respect to the primary fastening system. A secondary component may be discrete from the chassis or another feature in the respective waist region, or the secondary component may be integral with the chassis or another feature joined to the chassis of the respective waist region (e.g., landing zone) and may form a portion of a surface of the chassis or said feature.

In a particular example, secondary fastening components 210 may be hooks, and secondary receiving components 212 may be disposed on and/or formed from the wearer-facing sides of the back ears 34 serving as the loops component of a hook-and-loop fastening system. In one particular example, a wearer-facing layer forming a portion of the rear waist region may include a nonwoven material adapted to serve as a receiving component 212 and fastenably engage with hooks constituting the secondary fastening components 210. As described above with respect to the primary fastening component, the secondary fastening component may be a separate patch of material joined to the chassis or another component in the first waist region. Alternatively, a portion of the secondary fastening component may be integral with the chassis or said other component (e.g., landing zone substrate) that is disposed in the first waist region. As noted with the primary fastening component, the secondary fastening component may be produced via application of molten polymer resin onto the web material, and subsequent formation of hooks in and from the melted, applied resin via known methods. The secondary fastening components may be integrally formed from polymeric material by heating and softening a portion of the material and pressing it into hook-forming cavities, as is disclosed in U.S. Pat. No. 8,784,722. The secondary fastening components may be integrally formed from the polymeric material through a single continuous process as is disclosed in commonly assigned U.S. patent application Ser. No. 16/545,425.

Where integrally formed, the fastening elements may be formed from one or more layers of the article component as is disclosed in commonly assigned U.S. patent application Ser. No. 17/173,453. In some embodiments, two integral fastening elements in the fastening component may be formed from different material layers. Layers and materials from which integral fastening elements may be formed may comprise a nonwoven, elastomer, film, polyolefin (e.g., polypropylene, polyethlene), adhesive, ink, dye, tactile modifier (e.g., silicone) and combinations thereof. A layer may be applied in a liquid state or in at least a partially molten state to the overlapping region. In various nonlimiting examples, fastening elements are formed from resilient yet conformable materials such as polypropylene and/or polyethylene. Such resilient materials permit the fastening materials to return to their desired configuration after use or other disruption.

By integrally forming fastening elements, the practical constraints and/or costs presented by supply and application of strips of pre-manufactured fastening material are eliminated, and the areas of fastening elements may be provided in any desired configuration. It can be appreciated that areas of fastening elements may be configured in any desired size, shape, pattern, directionality of fastening, number of elements, or orientation. An orientation of an area of fastening elements is the angle of a line passing through the maximum dimension of the area with respect to the longitudinal axis of the article.

Further to the above, integral fastening components may be formed with varying directionality to provide different benefits in different sections of the component. For instance, hooks which are asymmetric about their vertical centerline (such that create an inverted J-shape or similar hook configuration) may be formed so that the open portion is pointed in the direction of expected engagement. In further nonlimiting examples, hooks in a front waist region 14 may be imparted with directionality approaching or along the lateral direction and extending toward the longitudinal axis of the diaper. Such directionality provides mechanical structure extending in a direction opposite the ordinary direction of shear forces (directed away from the longitudinal axis in the front region) that would be exerted on the hooks in that region while the hooks are engaged during wear, providing for added fastening strength and/or more secure attachment, as compared with non-directional hooks of similar size, material utilization (shape volume) and numerical density. Hooks in the rear waist region may be imparted with directionality toward the longitudinal axis of the diaper (when the fastening member is in the open position). Such directionality would oppose the ordinary direction of shear forces that would be exerted on the hooks in the front waist region when the hooks are engaged (i.e., fastened) during wear, providing for added fastening strength and/or more secure attachment, as compared with non-directional hooks of similar size, material utilization (shape volume) and numerical density.

In some embodiments, the primary and secondary fastening components are disposed on opposite surfaces (e.g., the primary fastening component is disposed on the wearer-facing surface and the secondary fastening component is disposed on the garment-facing surface). Likewise, the primary and secondary receiving components may be disposed on opposite surfaces.

In nonlimiting examples, the web material comprising the secondary fastening component (e.g., hooks) may also comprise the primary receiving component (e.g., loops). Additionally, or alternatively, the material comprising the primary fastening component (e.g., hooks) may also comprise the secondary receiving component (e.g., loops).

The primary and/or the secondary fastening component may comprise one or more pluralities of fastening elements, such as first plurality 301 and a second plurality 302 as shown in FIG. 2. Where multiple pluralities of elements exist in a fastening component, the pluralities may differ by: shapes of fastening elements, number of fastening elements, directionality of fastening elements, orientation of array, average spacing of fastening elements, whether fastening elements are discrete or integral or some combination, fastening element constituent materials, the number and/or types of layers from which integral fastening elements are formed, average size of fastening elements, aggregate shape of the array, surface area, opacity, color and combinations thereof. Each plurality may comprise fastening elements that are no more than about 2 mm, or from about 0.1 mm to about 2 mm, or from about 0.5 mm to about 1.5 mm apart from at least one of the other fastening elements in the plurality, reciting for each range every 0.1 mm increment therein. Pluralities may be distinguished from one another in that one plurality is at least about 2 mm or more, or about 2.25 mm or more, or about 35 mm or less, or about 30 mm or less, or about 25 mm or less, or about 15 mm or less, from about 2.25 mm to about 35 mm, or from about 3 mm to about 30 mm, or from about 2.5 mm to about 25 mm, or from about 3 mm to about 20 mm, or from about 4 mm to about 15 mm from a separate plurality, reciting for each range every 1 mm increment therein. A void area 326 separates pluralities of fastening elements as shown in FIG. 2. It is also contemplated that fastening elements in two different pluralities may be made from different materials and/or different fastening elements within the same plurality may be made from different materials. For instance, one plurality may comprise fastening elements comprising stiffer materials such as nylon, polyolefins and biocomponent coextruded materials (e.g., polypropylene/polyethylene) and combinations thereof, while another may comprise fastening elements formed from more flexible materials such as polymers blended with low modulus additives (e.g., oils, elastomers such as VISTAMAXX®).

Figure 3:
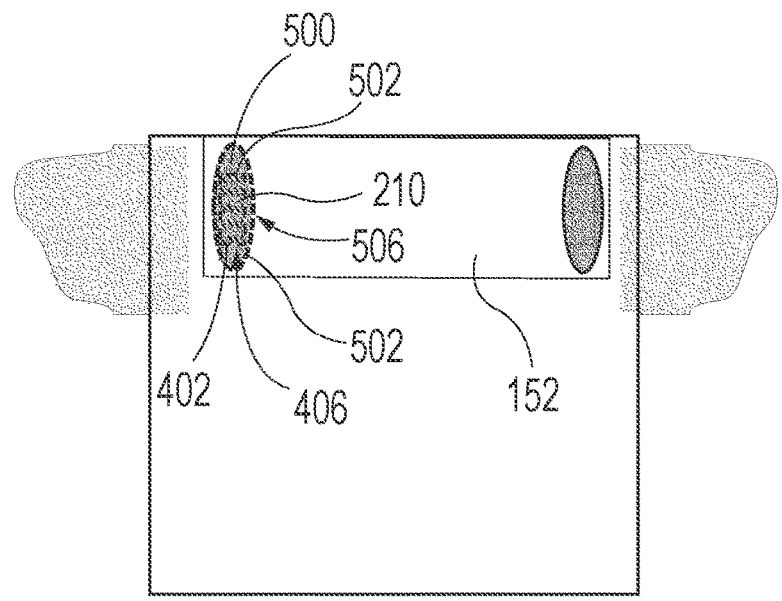
FIG. 3 is a schematic plan view of a portion of an exemplary absorbent article according to a nonlimiting embodiment.
Figure 4:
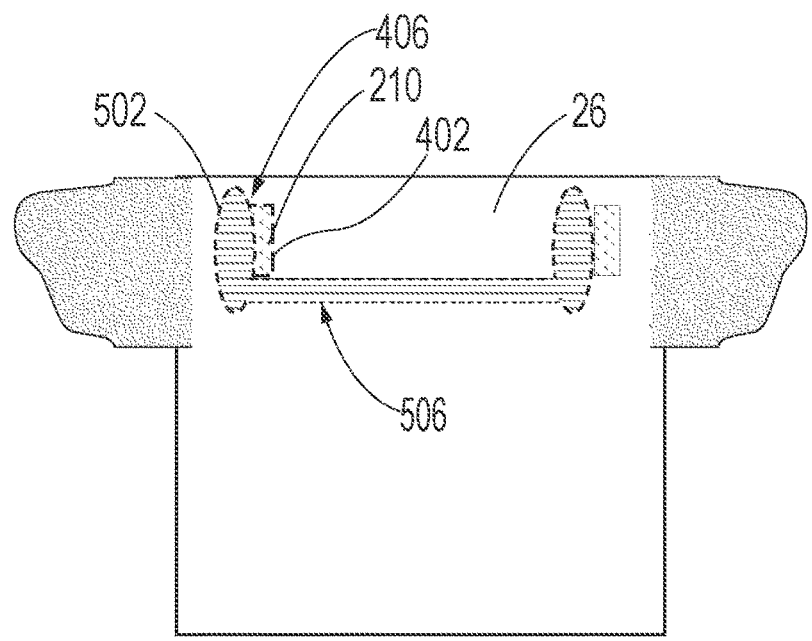
FIG. 4 is a schematic plan view of a portion of another exemplary absorbent article according to a nonlimiting embodiment.

In some embodiments, the article may comprise one or more fastening area graphics 500, fastening area graphics being graphics within 5 mm or less of a fastening component (e.g., the secondary fastening component 210), including graphics that fully or partially overlap the fastening component. Graphics may be formed through printing, tinting, colored adhesives, bonding, and combinations thereof. In nonlimiting examples, a fastening area graphic 500 at least partially overlaps the secondary fastening component. Turning to FIGS. 3-4, the fastening area graphic 500 comprises a graphic periphery 502. The fastening component comprises a fastening component periphery 402, which may differ from the graphic periphery by at least one of shape, size, area, and continuity/discontinuity. The periphery is determined by connecting, via imaginary lines, adjacent outward extents of applicable fastening area graphic or fastening component, to draw a boundary about the applicable graphic or fastening component. Where the graphic is discontinuous, segments within 2 mm of each other are assessed together when forming the periphery. Where the fastening component is discontinuous (i.e., multiple pluralities of fastening elements), pluralities within 10 mm of each other are assessed together when drawing the periphery. For instance, in FIGS. 3 and 4, the periphery is indicated as dotted line. In various embodiments, the fastening component periphery comprises a first shape 406 and the graphic periphery 502 comprises a second shape 506 different from the first shape 406. For instance, in FIG. 2, the first shape 406 (on the right side of the diaper when facing the viewer) is shown as an oval, and the second shape 506 is shown as a star. In FIG. 3, the first shape is a rectangle, and the second shape is an oval. In FIG. 4, the first shape is a rectangle and the second shape comprises two ovals connected by a line. Any suitable combination of shapes may be employed. In nonlimiting examples, the fastening component comprises one or more curvilinear segments. In further nonlimiting examples, the entire fastening component periphery is curvilinear. Additionally, or alternatively, the graphic periphery, or portions thereof, may be curvilinear.

The fastening component periphery 402 defines an fastening component area, which is the mathematical two-dimensional area within the periphery 402. Likewise, the graphic periphery 502 comprises a graphic area, which is the mathematical two-dimensional area within the periphery 502. In various embodiments, the graphic area is different than the fastening component area. The graphic area may be greater than the fastening component area. The graphic area may be greater than the fastening component area by at least about 10%, or at least about 20%, or from about 10% to about 50%, reciting for said range every 1% increment therein. Additionally, or alternatively, the graphic 500 may overlap the fastening component for at least about 20%, or at least about 35%, or at least about 50%, or from about 20% to about 100% of the fastening component area, reciting for said range every 5% increment therein.

In various embodiments, the fastening component is not visible. In other embodiments, the fastening component is visible but not readily distinguishable from surrounding areas. For instance, the fastening elements may be the same color as surrounding materials. Further still, the fastening component, or more particularly the fastening elements, may be relatively small. Providing a fastening area graphic may help the user to locate the fastening elements and/or position the components of the fastening system.

Figure 5:
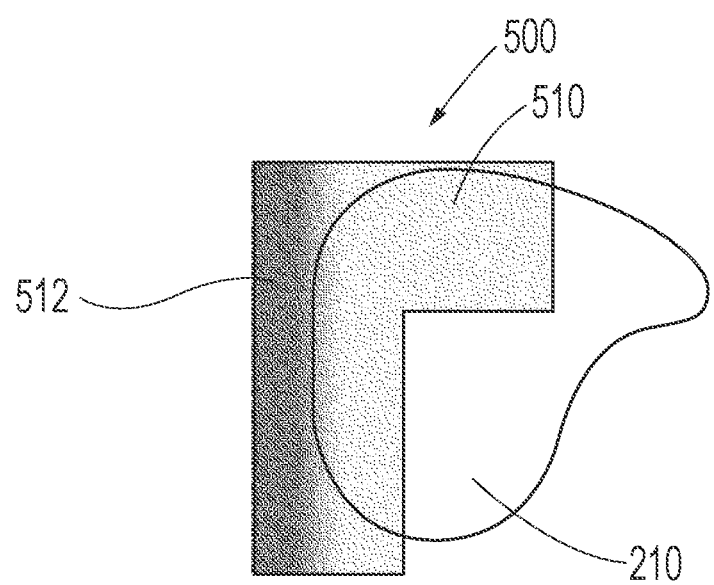
FIG. 5 is a schematic plan view of a fastening component according to a nonlimiting embodiment.

As discussed, the fastening area graphic 500 may at least partially overlap the fastening component. The graphic 500 may comprise a first portion 510 which overlaps the fastening component and a second portion 512 that is in non-overlapping relationship with the fastening component. The first portion may differ from the second portion by one of the following: color, color intensity, transparency/opacity, saturation, reflection, size, shape, print resolution and combinations thereof. For example, as shown in FIG. 5, the first portion may be more transparent than the second portion and thereby highlighting the area of the fastening elements. In some nonlimiting examples, the opacity of the second portion is about 15% greater, or about 25% greater, or about 30% greater or about 50% greater, or from about 25% to about 100% greater than the opacity of the first portion as determined by the Opacity Test Method. Additionally, or alternatively, the first portion may be more reflective than the second portion, reflecting more light and/or appearing shinier than the second portion and thereby highlighting the area of the fastening elements.

The first portion 510 may overlap the fastening component for at least about 20%, or at least about 35%, or at least about 50%, or from about 20% to 100% of the fastening component area, reciting for said range every 5% increment therein. In nonlimiting examples, a portion of the fastening component may extend outside of the graphic as shown for example in FIGS. 4-5.

Figure 6:
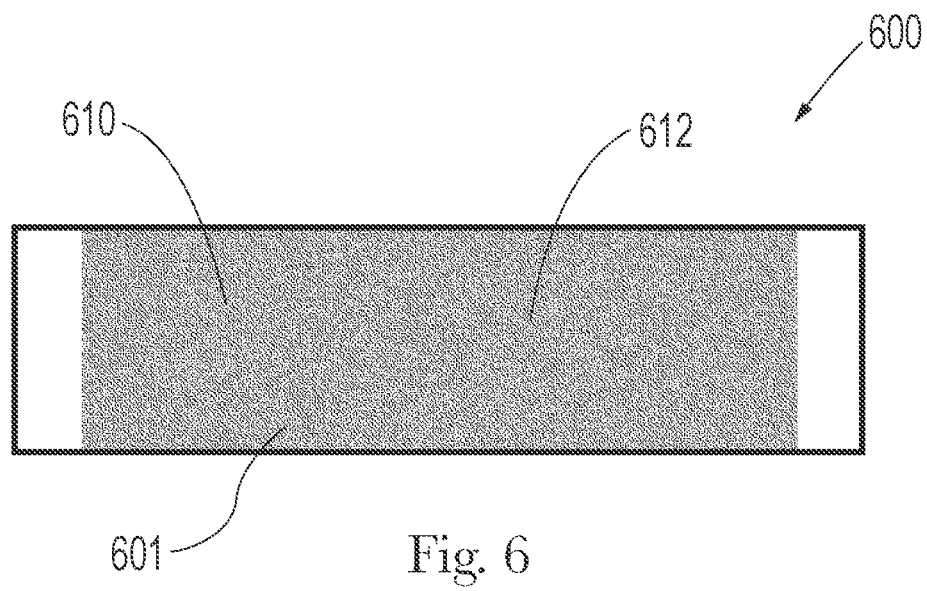
FIG. 6 is a schematic plan view of a substrate according to a nonlimiting embodiment.
Figure 7:
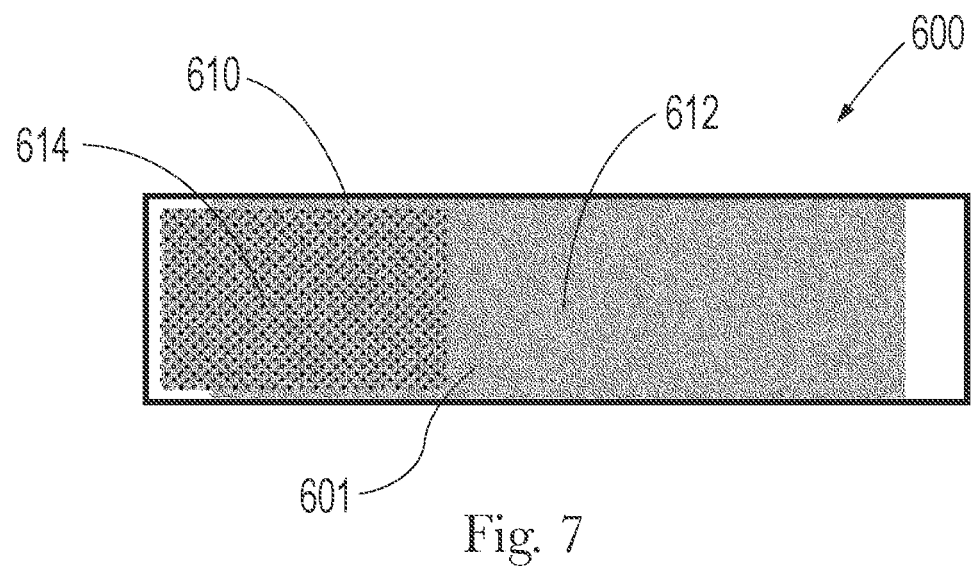
FIG. 7 is a schematic plan view of the substrate of FIG. 6 having a fastening component according to a nonlimiting embodiment.
Figure 8:
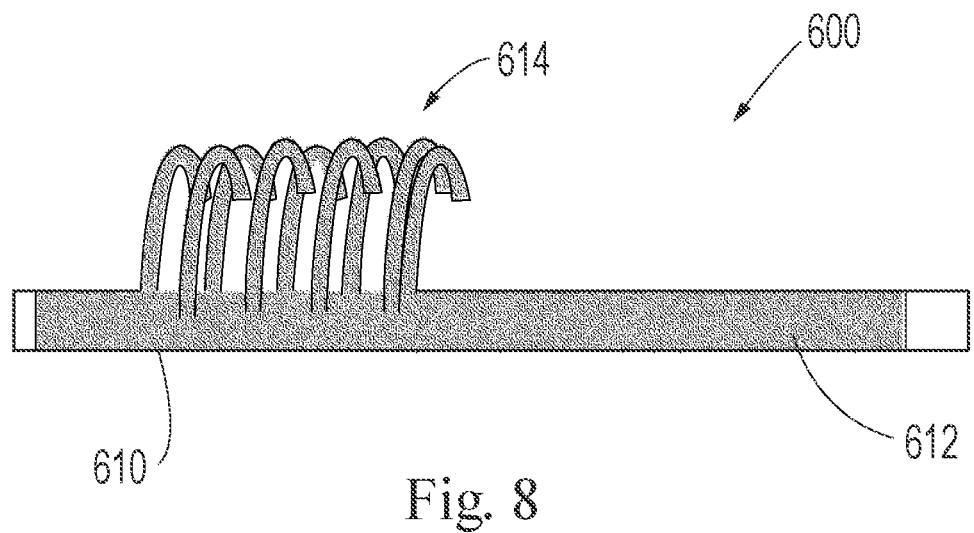
FIGS. 8-10 are schematic side elevation views of exemplary hook configurations according to nonlimiting embodiments.
Figure 9:
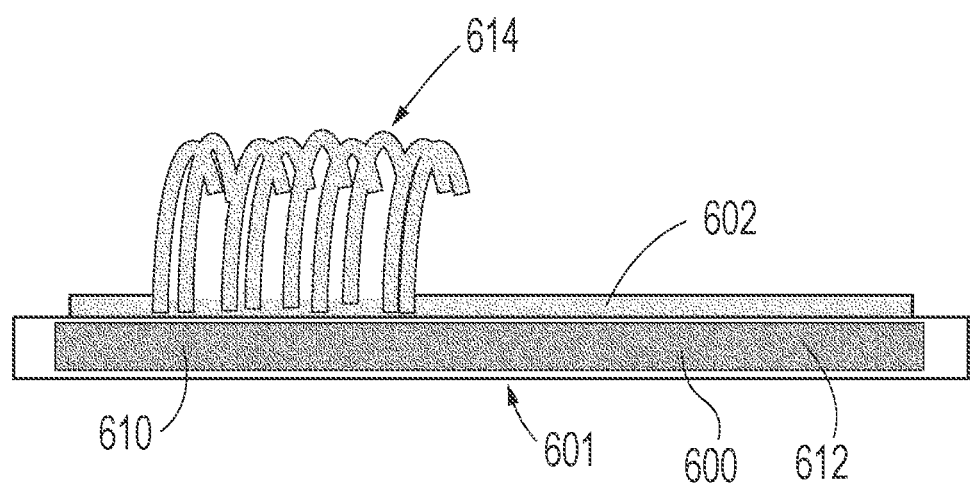

A difference in the first and second portion may be achieved through any suitable method. In certain embodiments, a method for forming a fastening component (e.g., the secondary fastening component 210, or the first fastening component 110) includes the steps of providing a substrate 600 having a colored portion 601. The colored portion is nominally divided into multiple portions, including a first portion 610 and a second portion 612 as shown in FIG. 6. The method further comprises overlapping a first plurality 614 of fastening elements with the first portion but not with the second portion. The first plurality may comprise integrally formed fastening elements. The step of overlapping the first plurality with the first portion may comprise integrally forming the first plurality from the substrate as illustrated in FIG. 8. The fastening elements may be formed by any suitable means including forming fastening elements by heating and softening a portion of material and pressing it into element-forming cavities, as is disclosed in U.S. Pat. No. 8,784,722. Additionally, or alternatively, the step of overlapping the first portion with the first plurality may comprise integrally forming the first plurality from a second substrate 602 and positioning the second substrate in overlapping relationship with the first portion as shown in FIG. 9. In nonlimiting examples, the second substrate comprises a color which may be different than the color of the colored portion. In this way, a third, blended color may be formed from the combination of the substrates 600, 602. The substrates 600, 602 may be joined by any suitable means. It is also contemplated that the fastening elements may be formed from the substrate 600 and the second substrate 602 as shown in FIG. 10.

The method may further comprises printing the substrate 600 to form the colored portion 601. Additionally, or alternatively, the method may comprise tinting the substrate 600 to form the colored portion.

In nonlimiting examples, the substrate 600 may comprise the backsheet 26 of an absorbent article. In further nonlimiting examples, the substrate 600 may be joined to a backsheet 26 by any suitable means. It is also contemplated that the substrate may be joined to the topsheet 24, an ear 30, a fastening arm 33 or any other suitable portion of an absorbent article. The substrate may be disposed in the first waist region 14. The substrate may be disposed in the second waist region 18.

Figure 10:
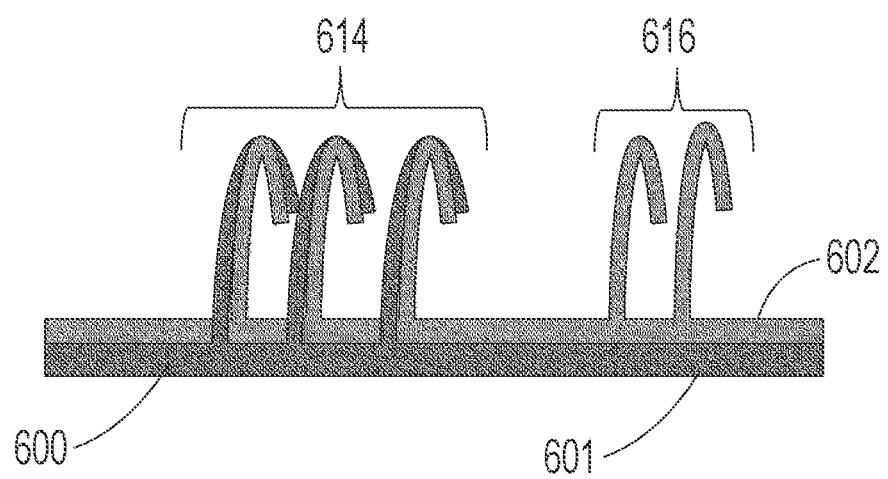

The method may further comprise forming a second plurality of fastening elements 616, which may be integrally formed from the second substrate 602 as illustrated in FIG. 10. The second plurality of fastening elements may differ from the first plurality by one of the following: shapes of fastening elements, number of fastening elements, directionality of fastening elements, orientation of array, average spacing of fastening elements, whether fastening elements are discrete or integral or some combination, fastening element constituent materials, the number and/or types of layers from which integral fastening elements are formed, average size of fastening elements, aggregate shape of the array, surface area, opacity, color and combinations thereof.

Figure 11:
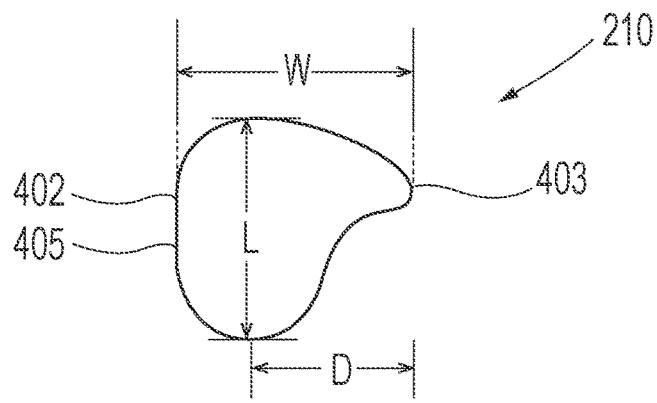
FIGS. 11-13 are schematic plan views of exemplary fastening component perimeters according to nonlimiting embodiments.
Figure 12:
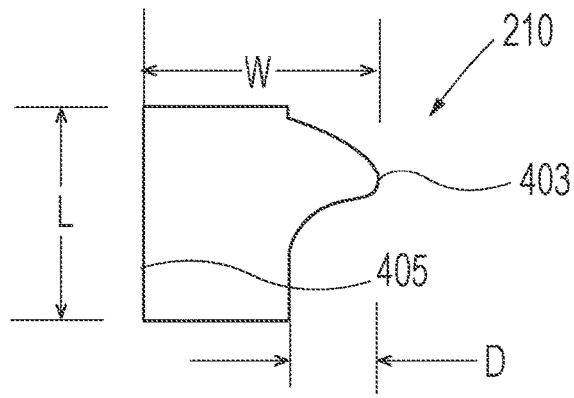
Figure 13:
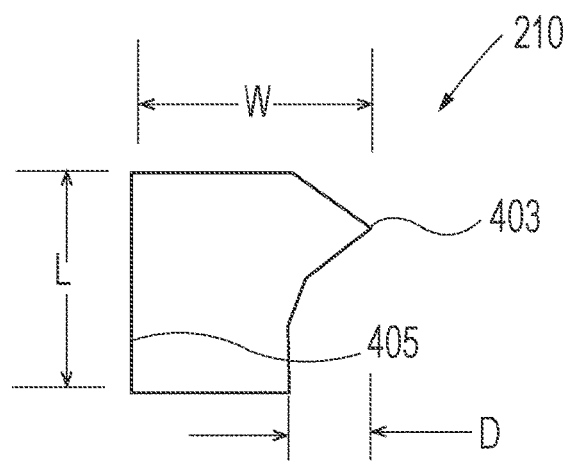

As noted, the fastening and receiving components may comprise any suitable shape or size. It may be desired to cut or otherwise impart one or more edges of secondary fastening components with rounded profiles, or profiles other than 90 degree corners, rather than sharp corners as shown in FIGS. 11 and 12 for example. This may be desirable for purposes of reducing chafing of the wearer's skin that might otherwise occur, through localized concentrations of pressure against the wearer's skin at sharp corners of components 210.

As noted, the fastening component comprises a periphery 402. As shown in FIG. 11, the fastening component periphery comprises an inboard-most extent 403 and outboard-most extent 405. The inboard-most extent 403 is the edge or point of the periphery that is closest to the longitudinal centerline 90 in an unfolded configuration 650. The outboard-most extent 405 is the edge or point of the periphery that is furthest from the longitudinal centerline 90 in an unfolded configuration 650. The fastening component periphery comprises a maximum longitudinal dimension, L, measured parallel to the longitudinal centerline and a maximum lateral dimension, W, measured parallel to the lateral centerline. In various embodiments, the fastening component periphery 402 is asymmetric. In such embodiments, the fastening component periphery may comprise a different longitudinal length at the inboard-most extent than at the outboard-most extent. Additionally, or alternatively, the fastening component periphery may comprise a nonuniform length (i.e., the length is not constant throughout the fastening component periphery's maximum width). The fastening component periphery may comprise a varying length (i.e., changing by, for example, sloping or curving) for a portion of the width, W. The fastening component periphery 402 may comprise a varying length throughout at least about 20%, or at least about 40%, or at least about 50%, or from about 20% to about 100%, or from about 40% to about 75% of the maximum width, W, reciting for each range every 5% increment therein. Additionally, or alternatively, the fastening component periphery may comprise a nonuniform width (i.e., the width is not constant throughout the fastening component periphery's maximum length). In nonlimiting examples, the fastening component periphery may comprise a varying width for a portion of the length, L. The fastening component periphery 402 may comprise a varying width throughout at least about 20%, or at least about 40%, or at least about 50%, or from about 20% to about 100%, or from about 40% to about 75% of the maximum length, reciting for each range every 5% increment therein.

In various embodiments, the maximum longitudinal dimension, L, is disposed laterally outboard of the inboard-most extent 403 as shown in FIGS. 11-14. The maximum longitudinal dimension, L, may be laterally outboard of the inboard-most extent 403 by a minimum separation distance D. The minimum separation distance, D, may be at least about 1 mm, or at least about 5 mm, or at least about 10 mm, or from about 1 mm to about 15 mm, reciting for said range every 1 mm increment therein. Additionally, or alternatively, the minimum separation distance, D, may be at least about 5%, or at least about 20%, or at least about 50%, or from about from about 5% to about 100%, or from about 10% to about 90% of the maximum lateral dimension, W, reciting for said ranges every 5% increment therein. In nonlimiting examples, the maximum longitudinal dimension may be coincident with the outboard-most extent 405 as show for example in FIG. 12.

Figure 14:
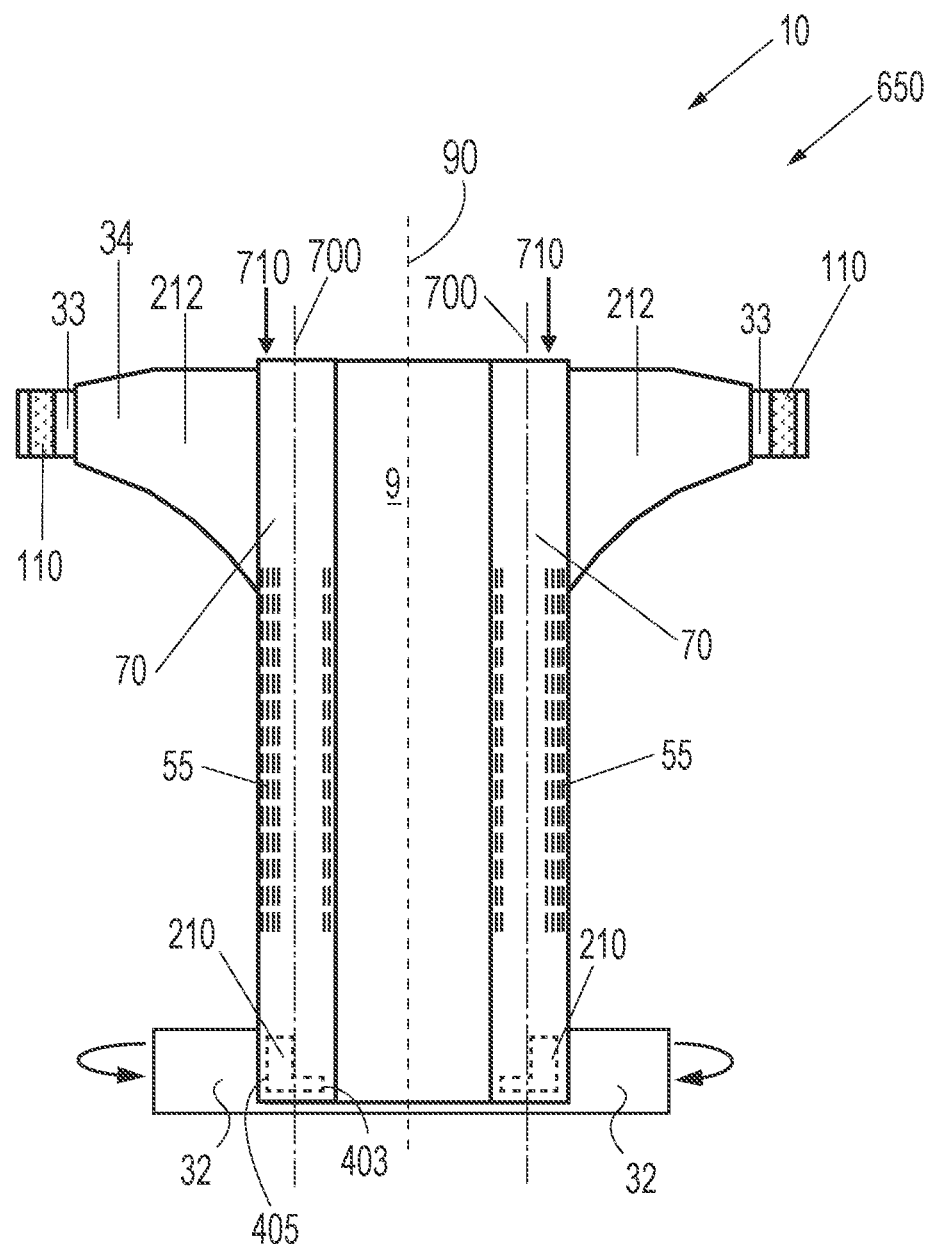
FIG. 14 is a schematic plan view of an exemplary absorbent article according to a nonlimiting embodiment. The absorbent article is shown in a flat, uncontracted state with the wearer-facing surface facing the viewer.

Turning to FIG. 14, where the maximum longitudinal dimension is disposed outboard of the inboard-most extent 403, the interaction between the primary and secondary fastening components (and their respective elements) can be minimized in an engaged configuration (i.e., when the fastening components are engaged with their receiving components). For example, configuring the secondary fastening component with the maximum longitudinal dimension outboard of the inboard-extent reduces the likelihood of the secondary fastening component interfering with the space available for engagement of the primary fastening component in the first waist region. Stated differently, the presence of a secondary fastening component could reduce the amount of space available for engagement of the primary fastening component. By shortening the length of the secondary fastening component at its inboard extent, more receiving area will be available for the primary fastening component despite the presence of the secondary fastening component. This configuration permits the article to fit a broader range of users than articles with known secondary fasteners, which limit the amount of receiving area. Further, it is believed that varying the length and/or the width of the fastening component periphery can provide for more precise targeting of fastening.

Figure 15:
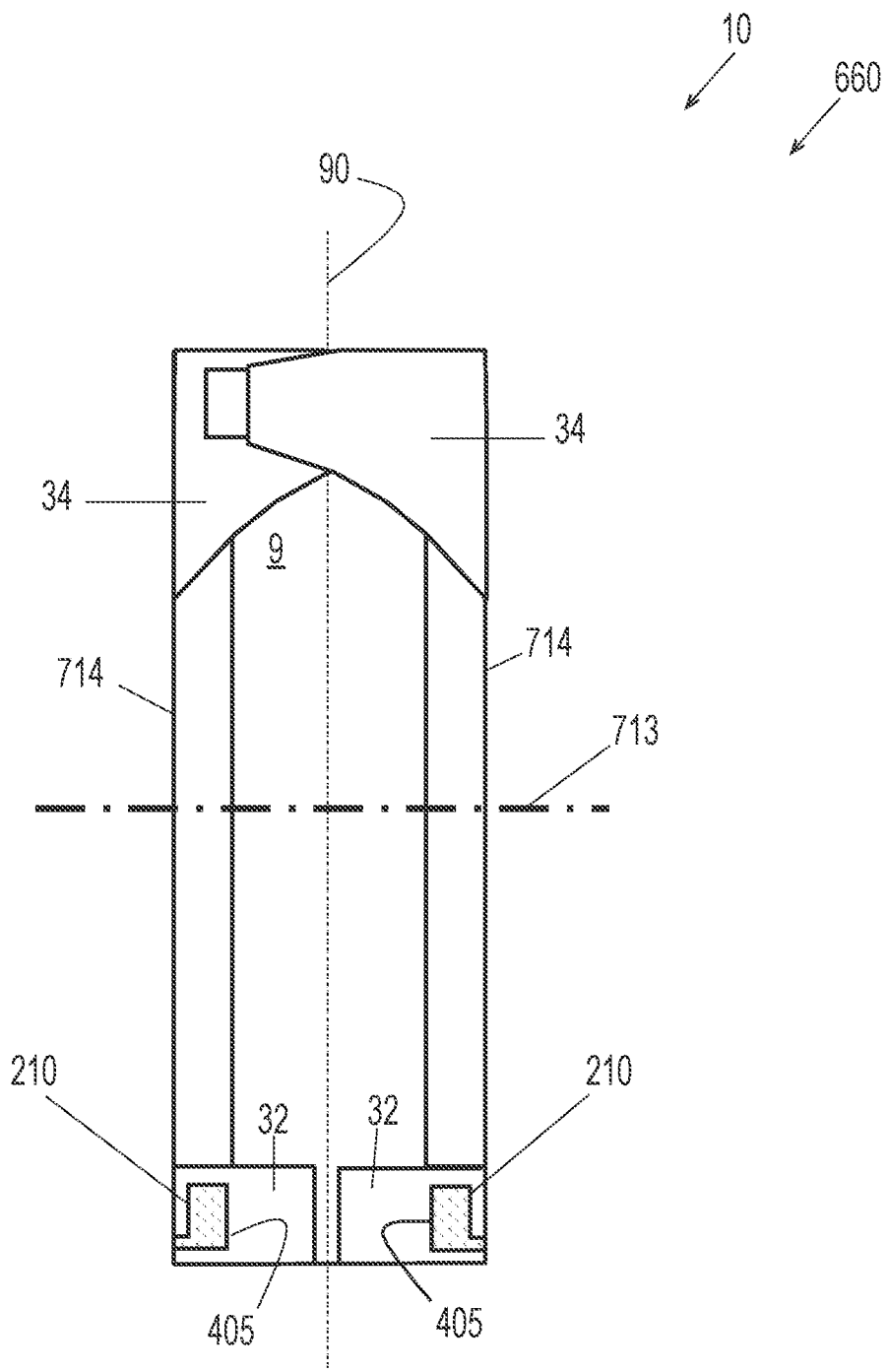
FIG. 15 is a schematic plan view of the absorbent article in FIG. 14 wherein the ears are in a folded configuration.

Still referring to FIG. 14, it may be desired to provide the absorbent article in a folded configuration for packaging, for example. As shown in FIG. 15, the waist regions may be folded laterally back over along longitudinal foldlines 700, such that in a folded configuration 660, the ears 30 are disposed laterally inboard of longitudinal edges 12. The ears, and other portions of the waist regions outboard of the foldline (in an unfolded configuration), may be folded towards the wearer-facing surface in an e-fold configuration as shown in FIG. 15. It is also contemplated that the ears and other waist regions may be folded towards the garment-facing surface.

Figure 16:
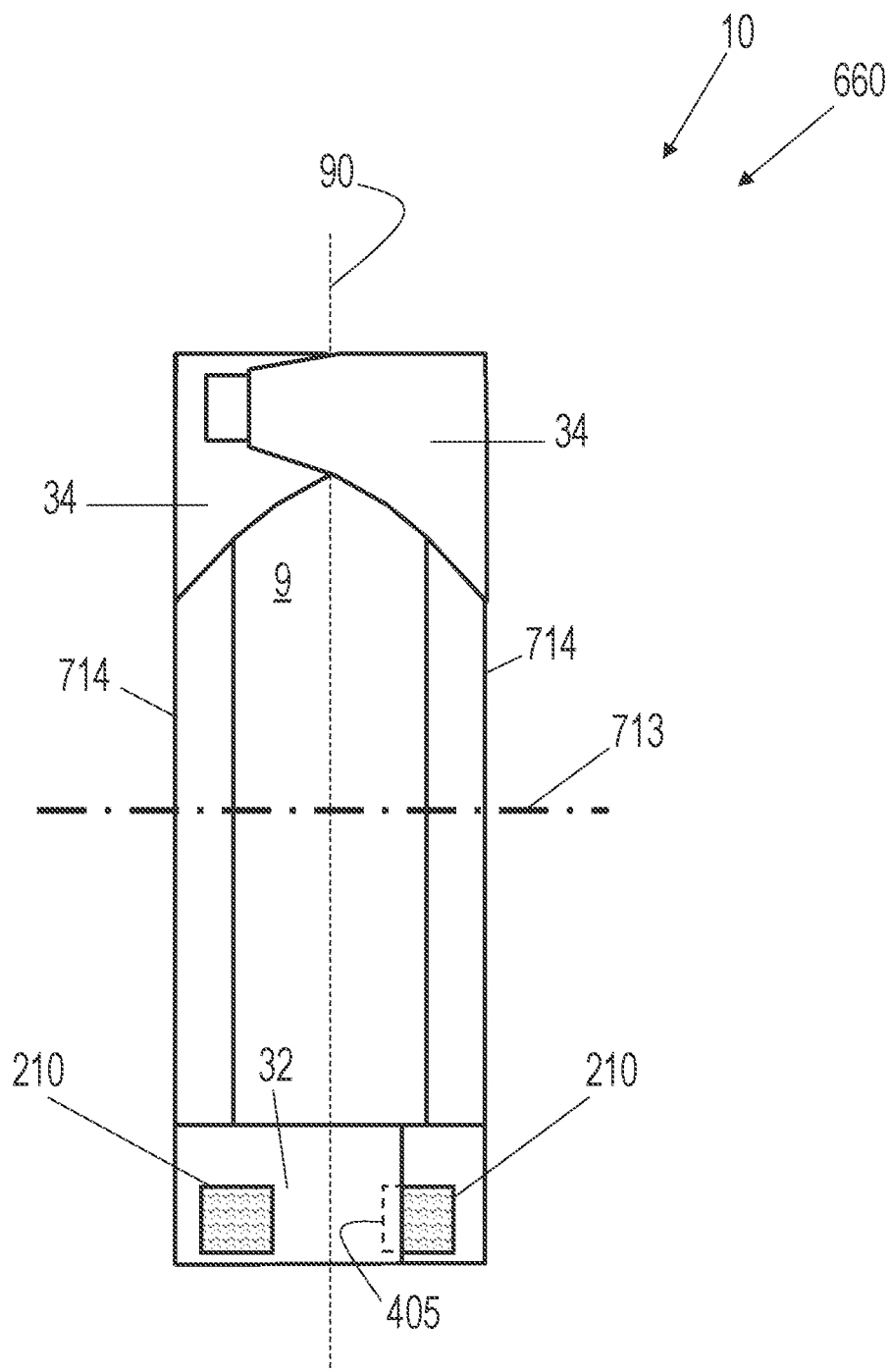
FIG. 16 is a schematic plan view of an exemplary absorbent article wherein the ears are in a folded configuration according to a nonlimiting embodiment.
Figure 17:
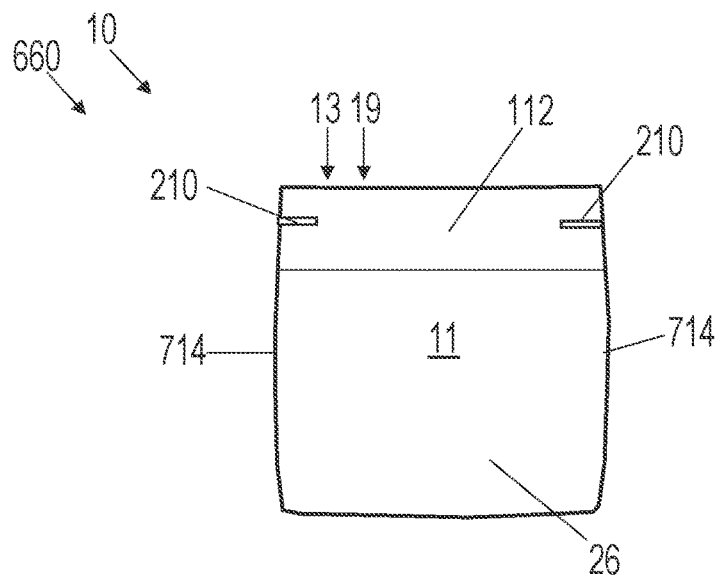
FIGS. 17-19 are schematic front plan views of exemplary absorbent articles in folded configurations according to nonlimiting embodiments.
Figure 18:
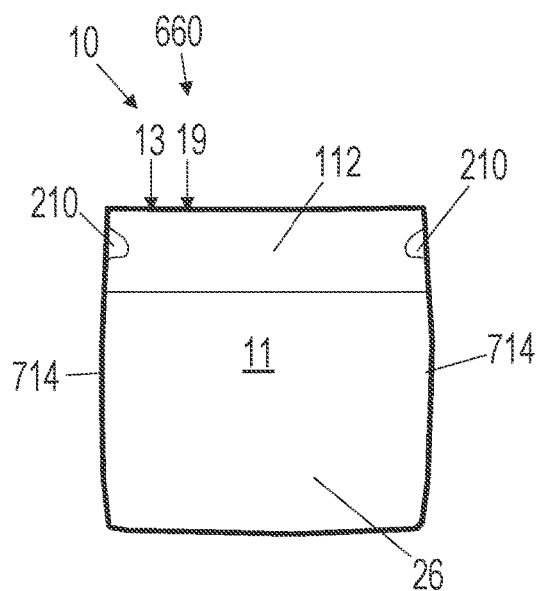
Figure 19:
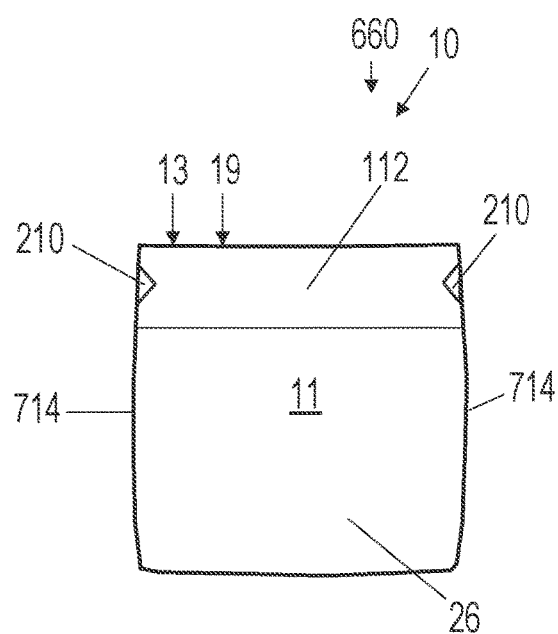

It is generally desirable that absorbent articles of the type contemplated herein be folded to a more compact configuration for efficient packaging and shipping. Accordingly, in a first step, left and right side margins 710 of the article may be folded laterally inwardly, about left and right longitudinal article folding lines 700 as indicated by the curving arrows in FIG. 14, to bring the article to a first interim folded configuration depicted in FIG. 15, with left and right longitudinal folded edges 714. FIG. 16 also depicts an article in an interim folded configuration with an overlapping first waist region. Referring to FIG. 17, in a next step, the article may be folded over on itself and approximately in half lengthwise, wearer-facing surfaces in, about a lateral fold line 713, to bring it into a folded article configuration as shown in FIG. 17, which is a neat and compact configuration suitable for efficient stacking of a plurality of absorbent articles, packaging and shipment. FIGS. 18 and 19 also depict articles folded over themselves approximately in half with different secondary fastening peripheries.

A folded configuration may provide several advantages. First, it provides for control over the ears 30 as the chassis moves through any further downstream processing, folding and/or packaging, reducing chances that ears 30 will snag in any equipment, with possible resulting damage. Second, where secondary fastening components 210 are included, folding the ears 32 (or other portions of the waist region) over portions of one or more secondary fastening components 210 will shield and protect the secondary fastening components from unwanted contact and interaction with other portions of the article prior to its use. For example, where secondary fastening components 210 are patches of hooks material, it may be undesirable to have large portions of the fasteners exposed when, for example, the entire diaper is folded for packaging because they may undesirably snag and/or undesirably attach to other portions of the article in such folded article configuration. All or a portion of a secondary fastening component may be covered by, for example, overlapping one side of the article over the other (e.g., overlapping the left side over the right side) as shown in FIG. 16, or by folding one side over itself in a z-fold configuration.

The inboard-most extent 403 of a secondary fastening component may be coincident with or even disposed inboard of the article foldline 700. The inboard-most extent 403 of the secondary fastening component periphery may be disposed in overlapping relationship with the foldline 700, or may be disposed at least about 2 mm, or at least about 5 mm, or from about 0 mm to about 10 mm, or from about 2 mm to about 5 mm laterally inboard of the article longitudinal foldline 700.

In embodiments where the fastening component periphery comprises a nonuniform length as shown in FIGS. 14-15 for example, the maximum longitudinal dimension may be disposed outboard of the article foldline 700 while the inboard-most extent 403 may be disposed inboard of the article foldline. Without being bound by theory, it is believed that such configuration minimizes undesirable effects from the fastening elements being disposed on the front of the diaper in a folded, unengaged configuration as shown in FIG. 17 while maintaining suitable fastening area for the secondary fastening component as well as the primary fastening component.

Figure 20:
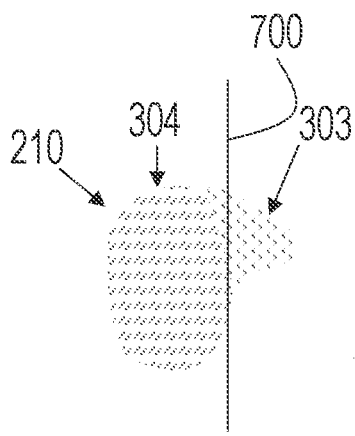
FIG. 20 is a schematic plan view of a fastening component according to a nonlimiting embodiment.

As noted, the fastening periphery comprises a fastening component area (i.e., two-dimensional area). In various nonlimiting examples, at least about 50%, or at least about 60%, or at least about 75%, or from about 20% to about 100%, or from about 25% to about 90%, or from about 30% to about 75% of the fastening component area is disposed outboard of the article longitudinal foldline, reciting for each range every 5% increment therein. In various embodiments, a greater number of fastening elements is disposed outboard of the article foldline than inboard of the article foldline. For instance, as shown in FIG. 20, a fastening component may comprise a plurality of fastening elements disposed laterally inboard of the article longitudinal foldline (hereinafter an inboard plurality 303) and a plurality of fastening elements disposed outboard of the article longitudinal foldline 700 (hereinafter an outboard plurality 304). The outboard plurality may comprise a greater number of fastening elements than the inboard plurality.

Figure 21:
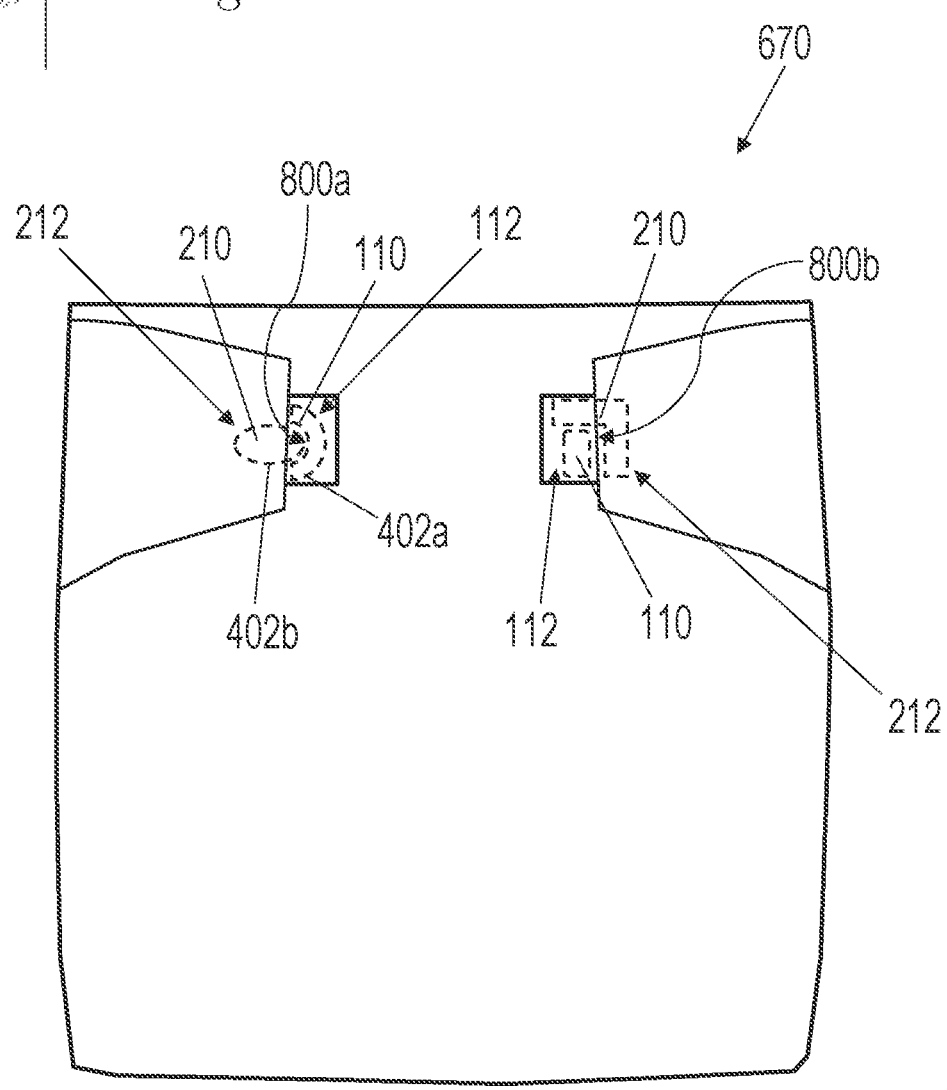
FIG. 21 is a schematic front plan view of an exemplary absorbent article in a folded configuration according to a nonlimiting embodiment.
Figure 22:
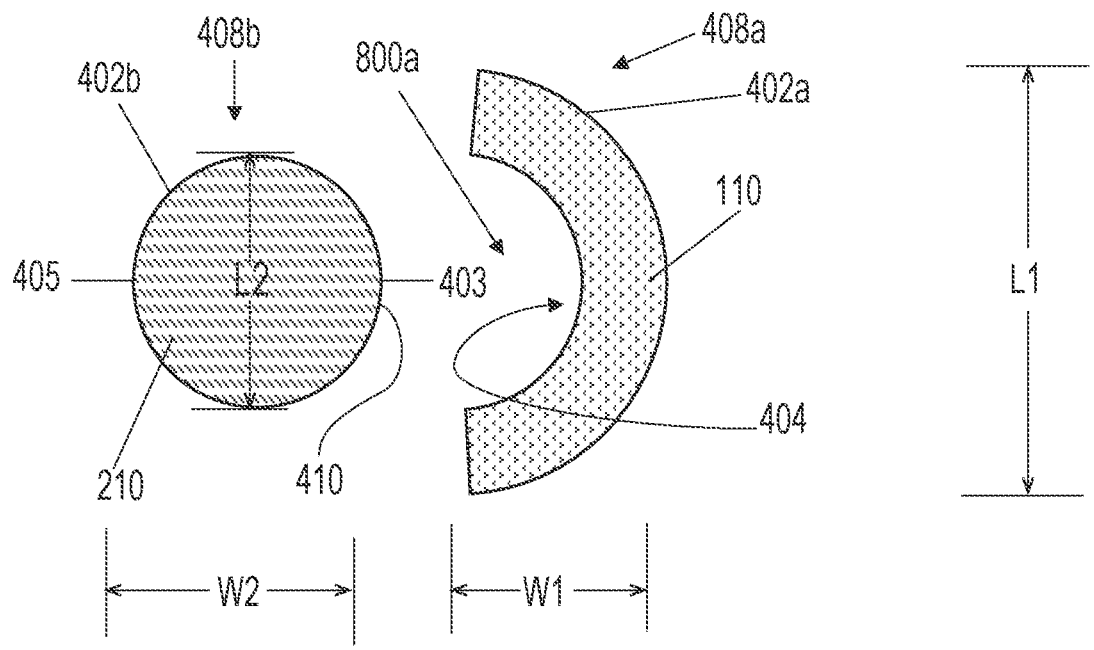
FIGS. 22-23 are schematic plan views of the fastening components of the absorbent article in FIG. 21.
Figure 23:
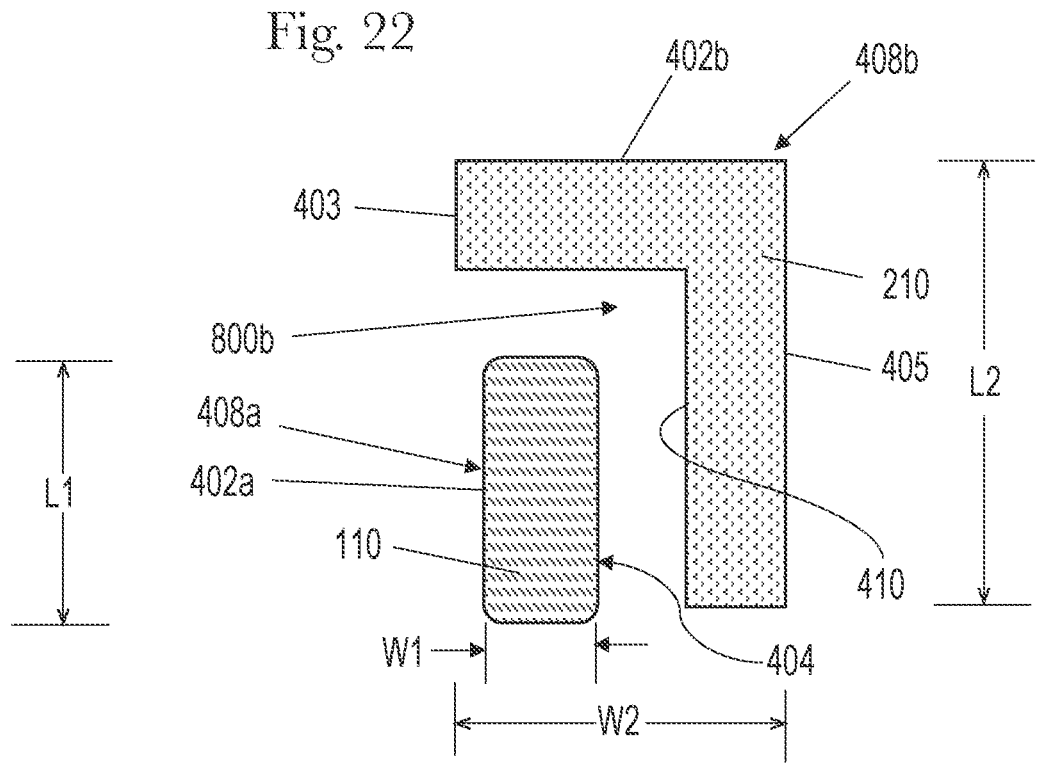

Turning to FIG. 21, when the article 10 is positioned in an engaged configuration 670, when the fastening components are engaged with the receiving components as designed, the primary fastening component periphery 402a may form a pocket 800a for the secondary fastening component 210, and/or the secondary fastening component periphery 402b may form a pocket 800b for the primary fastening component 110. In such embodiments, the paired primary and secondary fastening components are disposed on the same side of the longitudinal centerline. As show in FIGS. 22-23, the pocket may comprise one or more edges that are complementary (i.e., fits with) edge(s) of the remaining fastening component. For instance, an interior side 404 of a primary fastening component periphery 402a may be complementary with inboard side 410 of the secondary fastening component periphery 402b. Complementary sides may comprise the same or similar curvature, angles, shapes and combinations thereof. In embodiments having a primary pocket 800a, a portion of the primary fastening component may be disposed longitudinally outboard of the entire secondary fastening component in the engaged configuration as shown in FIG. 22 (depicting the left side of the article of FIG. 21). Likewise, in embodiments comprising a secondary pocket 800b, a portion of the secondary fastening component may be disposed longitudinally outboard of the entire primary fastening component as shown in FIG. 23 (depicting the right side of the article of FIG. 21). It is also contemplated that a primary pocket may be formed such that a portion of the primary fastening component may be disposed longitudinally inboard of the entire secondary fastening component, and/or a secondary pocket may be formed such that a portion of the secondary fastening component may be disposed longitudinally inboard of the entire primary fastening component. In the area of the pocket, the fastening elements in the primary fastening component may be completely outside of the secondary fastening periphery in an engaged configuration.

The primary fastening component periphery 402a may comprise a first shape 408a, and the secondary fastening component periphery 402b may comprise a second shape 408b as shown in FIGS. 21-23 for example. The first and second shapes may differ. The primary fastening component periphery may comprise different dimensions than the secondary fastening component. For instance, the primary fastening component may comprise a maximum longitudinal dimension, $L1$, that is greater than the maximum longitudinal dimension of the secondary fastening component, $L2$, or vice versa. The primary fastening component may comprise a maximum lateral dimension, $W1$, that is greater than the maximum lateral dimension of the secondary fastening component, $W2$, or vice versa. Varying the dimensions can aid in designing the fastening components to complement one another.

As discussed above, a secondary fastening component 210 may be disposed on a primary receiving component. The primary receiving component comprises a receiving component area (i.e., the two-dimensional area). The fastening component area of the secondary fastening component may comprise about 20% or less, or about 15% or less, or about 5% or less, or from about 2% to about 20%, or from about 5% to about 15% of the receiving component area, reciting for said range every 1% increment therein. In this way, there remains ample area for engaging the primary fastening component, despite the presence of the secondary fastening component.

Leg Gasketing Systems

Returning to FIG. 1, the absorbent article 10 may comprise a leg gasketing system 70 attached to the chassis 20, which may comprise one or more cuffs. The leg gasketing system may comprise a pair of barrier leg cuffs 72. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge joined directly or indirectly to the topsheet 24 and/or the backsheet 26 and a free terminal edge 75, which is intended to contact and form a seal with the wearer's skin. In some embodiments, the free terminal edge 75 comprises a folded edge. The barrier leg cuffs 72 extend at least partially between the front waist edge 13 and the rear waist edge 19 of the absorbent article on opposite sides of the longitudinal centerline 90 and are at least present in the crotch region. The barrier leg cuffs may be joined at the proximal edge with the chassis of the article by a bond which may be made by gluing, fusion bonding, or a combination of other suitable bonding processes.

The barrier leg cuffs may be integral with the topsheet 24 or the backsheet 26 or may be a separate material joined to the article's chassis. Each barrier leg cuff 72 may comprise one, two or more elastic elements 55 close to the free terminal edge 75 to provide a better seal.

In addition to the barrier leg cuffs 72, the article may comprise gasketing cuffs 76, which are joined to the chassis of the absorbent article, in particular to the topsheet 24 and/or the backsheet 26 and are placed externally relative to the barrier leg cuffs 72. The gasketing cuffs 76 may provide a better seal around the thighs of the wearer. A gasketing cuff may comprise a proximal edge and a free terminal edge 77. The free terminal edge 77 may comprise a folded edge. Each gasketing cuff may comprise one or more elastic elements 55 in the chassis of the absorbent article between the topsheet 24 and backsheet 26 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs. Suitable leg gasketing systems which may be part of the absorbent article are disclosed in U.S. Pat. App. No. 62/134,622, 14/077,708; U.S. Pat. Nos. 8,939,957; 3,860,003; 7,435,243; 8,062,279.

Combinations

A. An absorbent article comprising:
   a first waist region, a second waist region, a crotch region disposed between the first and second waist regions;
   a topsheet, a backsheet, and an absorbent core disposed between the topsheet and backsheet;
   a primary fastening system and secondary fastening system, wherein the primary fastening system comprises a primary fastening component disposed in the second waist region and a primary receiving component disposed in the first waist region and operatively engageable with the primary fastening component; and wherein the secondary fastening system comprises a secondary fastening component disposed in the first waist region and a secondary receiving component disposed in the second waist region and operatively engageable with the secondary fastening component; and
   a graphic disposed in the first waist region in at least partial overlapping relationship with the secondary fastening component;
   wherein the secondary fastening component comprises a fastening component periphery having a first shape and a fastening component area, and the graphic comprises a graphic periphery having a second shape and a graphic area, wherein the first and second shapes are different.

B. The absorbent article of paragraph A, wherein the graphic overlaps at least 20%, or at least 50%, of the fastening component area.

C. The absorbent article of paragraphs A or B, wherein the secondary fastening component is not visible.

D. The absorbent article of any of the preceding paragraphs, wherein the secondary fastening component is disposed on the primary receiving component.

E. The absorbent article of any of the preceding paragraphs, wherein the secondary fastening component comprises fastening elements integrally formed from the backsheet and/or from the primary receiving component.

F. The absorbent article of any of the preceding paragraphs, wherein the graphic area is different than fastening component area.

G. The absorbent article of paragraph F, wherein the graphic area is greater than the fastening component area.

H. The absorbent article of any of the preceding paragraphs, wherein a first portion of the graphic overlaps the secondary fastening component and a second portion of the graphic does not overlap the secondary fastening component.

I. The absorbent article of paragraph H, wherein the first portion differs from the second portion by one of the following: color, color intensity, transparency, reflection, saturation, two-dimensional area, shape, print resolution and combinations thereof.

J. The absorbent article of paragraph I, wherein the second portion comprises an opacity that is at least 15% greater than an opacity of the first portion.

K. An absorbent article comprising:
   a first waist region, a second waist region, a crotch region disposed between the first and second waist regions;
   a topsheet, a backsheet, and an absorbent core disposed between the topsheet and backsheet;
   a primary fastening system and secondary fastening system, wherein the primary fastening system comprises a primary fastening component disposed in the second waist region and a primary receiving component disposed in the first waist region and operatively engageable with the primary fastening component; and wherein the secondary fastening system comprises a secondary fastening component disposed in the first waist region and a secondary receiving component disposed in the second waist region and operatively engageable with the secondary fastening component; and
   a graphic disposed in the first waist region in partial overlapping relationship with the secondary fastening component, such that a first portion of the graphic overlaps the secondary fastening component and a second portion of the graphic does not overlap the secondary fastening component;
   wherein the first portion differs from the second portion by one of the following: color, color intensity, transparency, reflection, saturation, two-dimensional area, shape, print resolution and combinations thereof.

L. The absorbent article of paragraph K, wherein the second portion comprises an opacity that is at least 15% greater than an opacity of the first portion.

M. The absorbent article of paragraphs K or L, wherein the first portion and second portion differ in color intensity.

N. The absorbent article of any of paragraphs K-M, wherein the secondary fastening component comprises a fastening component area and the first portion overlaps at least 20% of the fastening component area.

O. The absorbent article of paragraph N, wherein the first portion overlaps at least 50% of the fastening component area.

P. The absorbent article of any of paragraphs K-O, wherein the secondary fastening component is not visible.

Q. The absorbent article of any of the paragraphs K-P, wherein the secondary fastening component is disposed on the primary receiving component.

R. The absorbent article of any of the paragraphs K-Q, wherein the secondary fastening component comprises fastening elements integrally formed from the backsheet and/or from the primary receiving component.

S. The absorbent article of any of the paragraphs K-R, wherein the graphic comprises a graphic area and the fastening component comprises a fastening component area, and wherein the graphic area is different than fastening component area.

T. The absorbent article of paragraph S, wherein the graphic area is greater than the fastening component area.

U. A method of forming a fastening component comprising the steps of:

providing a substrate having a colored portion having a first portion and a second portion;

providing a first plurality of fastening elements; and overlapping the first plurality of fastening elements with the first portion but not the second portion, such that the second portion is void of the first plurality of fastening elements.

V. The method of paragraph U, wherein the first plurality of fastening elements comprise integrally formed fastening elements.

W. The method of paragraphs U or V, wherein the step of overlapping the first plurality of fastening elements with the first portion comprises integrally forming the first plurality of fastening elements from the first portion of the colored portion.

X. The method of any of paragraphs U-W, wherein the step of overlapping the first plurality of fastening elements with the first portion comprises integrally forming the first plurality of fastening elements from a second substrate and overlapping the second substrate with the first portion.

Y. The method of paragraph X, wherein the second substrate comprises a color.

Z. The method of any of paragraphs U-Y further comprising the step of integrally forming a second plurality of fastening elements from the second portion, wherein the second plurality differs from the first plurality by one of the following: shapes of fastening elements, number of fastening elements, directionality of fastening elements, orientation of array, average spacing of fastening elements, whether fastening elements are discrete or integral or some combination, fastening element constituent materials, the number and/or types of layers from which integral fastening elements are formed, average size of fastening elements, aggregate shape of the array, surface area, opacity, color and combinations thereof.

AA. The method of any of claims U-Z further comprising printing the substrate to form the colored portion.

BB. The method of any of claims U-AA further comprising tinting the substrate to provide the colored portion.

Test Methods

Hysteresis Test

The following test method utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23 deg. C.+−2 deg. C. and relative humidity of 50%+−%±2%. The samples are conditioned for 24 hours prior to testing.

1. Select a 2.54 cm (width), 7.62 cm (length) sample of the material for testing. In some cases, if it is not be possible to get a 2.54 cm×7.62 cm sample, a smaller sample may be used, but a gage length of 25 mm must still be used. If the sample is activated or includes an activation portion, the length of the sample is taken in the direction of activation.

2. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.

3. Calibrate the tester according to the manufacturer's instructions.

4. Set the distance between the grips at 25 mm.

5. Place the sample in the flat surface of the jaws such that the longitudinal axis of the sample is substantially parallel to the gauge length direction. Mount the sample with minimal slack. Set the slack preload at 0.02 N/cm. This means that the data collection starts when the slack is removed with a force of 0.02 N/cm. Strain is calculated based on the adjusted gauge length (lini), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100%.

6(a) First cycle loading: Pull the sample to a strain of 50% at a constant cross head speed of 254 mm/min.

6(b) First cycle unloading: Hold the sample at 50% strain for 30 seconds and then return the crosshead to its starting position (0% strain) at a constant cross head speed of 254 mm/min. Hold the sample in the unstrained state for 1 minute.

6(c) Set from second cycle loading: Pull the sample at a constant cross head speed of 254 mm/min, till it reaches a load of 0.05 N/25.4 mm (0.020 N/cm). Record the extended gauge length (lext). Next, return the crosshead to its starting position (zero strain) at a constant cross head speed of 254 mm/min. Set is defined as the strain at a second cycle load of 0.05 N/25.4 mm (0.020 N/cm). Calculate % set as indicated below.

6(d) Second cycle unload: Next, return the crosshead to its starting position (zero strain) at a constant cross head speed of 254 mm/min.

Percent Set is defined as the percent strain at a second cycle load of 0.05 N/25.4 mm (0.020 N/cm). Calculate % set as indicated below.

A computer data system records the force exerted on the sample during the test as a function of applied strain. From the resulting data generated, the following quantities are reported (note that loads are reported as force divided by the width of the sample and do not take into account the thickness of the sample):

1. Loads at 25% strain and 50% strain (N/cm)

2. % set (Percent Strain measured at a second cycle load force of 7 gram-force ($l_{ext}$) to the nearest 0.001 mm.

iv. % Set, which is defined as $(l_{ext}-l_{ini})/(l_{max}-l_{ini})*100\%$ to the nearest 0.01%.

The testing is repeated for six separate samples and the average and standard deviation reported.

Opacity Test Method

Opacity by contrast ratio measurements are made using a 0°/45° spectrophotometer suitable for making standard CIE L*a*b* color measurements (e.g. Hunterlab Labscan XE spectrophotometer, Hunter Associates Laboratory Inc., Reston Va. or equivalent). The diameter of the instrument's measurement port should be chosen such that only the region of interest is included within the measurement port. Analyses are performed in a room controlled at about 23° C.±2 C.° and 50%±2% relative humidity. Samples are conditioned at the same condition for 2 hours before testing.

Calibrate the instrument per the vendor instructions using the standard black and white tiles provided by the vendor. Set the spectrophotometer to use the CIE XYZ color space, with a D65 standard illumination and 10° observer. Using cryogenic spray and scissors carefully excise the specimen from the article for testing. Place the specimen flat against the instrument with the outward facing surface toward the spectrophotometer's measurement port and the region of interest within the port. Ensure that no tears, holes or apertures are within the measurement port. Place the white standard tile onto the opposing surface of the specimen such that it completely covers the measurement port. Take a reading for XYZ and record to 0.01 units. Without moving the specimen, remove the white plate and replace it with the black standard plate. Take a second reading for XYZ and record to 0.01 units. Repeat this procedure at a corresponding site for a total of ten (10) replicate specimens.

Opacity is calculated by dividing the Y value measured using the black tile as backing, divided by the Y value measured using the white tile as backing. Record the opacity value to the nearest 0.001. Calculate opacity for the 10 replicates for the sample and report the average opacity to the nearest 0.001.

The difference between an opacity of a first sample and a second sample is calculated using the following equation:

$$\% \text{ Difference} = \frac{\text{average opacity for sample 1} - \text{average opacity of sample 2}}{\text{average opacity of sample 2}} * 100\%$$

wherein sample 2 is the sample having the lower of the two average opacities.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising: a first waist region, a second waist region, a crotch region disposed between the first and second waist regions; a topsheet, a backsheet, and an absorbent core disposed between the topsheet and backsheet; a primary fastening system and secondary fastening system, wherein the primary fastening system comprises a primary fastening component disposed in the second waist region and a primary receiving component disposed in the first waist region and operatively engageable with the primary fastening component; and wherein the secondary fastening system comprises a secondary fastening component disposed in the first waist region and a secondary receiving component disposed in the second waist region and operatively engageable with the secondary fastening component; a longitudinal foldline disposed substantially parallel to a longitudinal axis of the absorbent article about which a portion of the first waist region and/or a portion of the second waist region is folded laterally back over itself when the absorbent article is in a folded configuration; and a graphic disposed in the first waist region in at least partial overlapping relationship with the secondary fastening component; wherein the secondary fastening component comprises a maximum longitudinal dimension, and wherein the maximum longitudinal dimension of the secondary fastening component is disposed outboard of an inboard-most extent of the secondary fastening component; and wherein in an unfolded configuration, the maximum longitudinal dimension of the secondary fastening component is disposed outboard of the longitudinal foldline and the inboard-most extent of the secondary fastening component is disposed inboard of the longitudinal foldline.

2. The absorbent article of claim 1, wherein the secondary fastening component comprises a fastening component area and wherein the graphic overlaps at least 20% of the fastening component area.

3. The absorbent article of claim 1, wherein the secondary fastening component is not visible.

4. The absorbent article of claim 1, wherein the secondary fastening component is disposed on the primary receiving component.

5. The absorbent article of claim 1, wherein the secondary fastening component comprises fastening elements integrally formed from the backsheet and/or from the primary receiving component.

6. The absorbent article of claim 1, wherein the secondary fastening component comprises a fastening component area and wherein the graphic comprises a graphic area and wherein the graphic area is different than fastening component area.

7. The absorbent article of claim 6, wherein the graphic area is greater than the fastening component area.

8. An absorbent article comprising: a first waist region, a second waist region, a crotch region disposed between the first and second waist regions; a topsheet, a backsheet, and an absorbent core disposed between the topsheet and backsheet; a primary fastening system and secondary fastening system, wherein the primary fastening system comprises a primary fastening component disposed in the second waist region and a primary receiving component disposed in the first waist region and operatively engageable with the primary fastening component; and wherein the secondary fastening system comprises a secondary fastening component disposed in the first waist region and a secondary receiving component disposed in the second waist region and operatively engageable with the secondary fastening component; a longitudinal foldline disposed substantially parallel to a longitudinal axis of the absorbent article about which a portion of the first waist region and/or a portion of the second waist region is folded laterally back over itself when the absorbent article is in a folded configuration; and a graphic disposed in the first waist region in partial overlapping relationship with the secondary fastening component, such that a first portion of the graphic overlaps the secondary fastening component and a second portion of the graphic does not overlap the secondary fastening component; wherein the secondary fastening component comprises a maximum longitudinal dimension, and wherein the maximum longitudinal dimension of the secondary fastening component is disposed outboard of an inboard-most extent of the secondary fastening component; and wherein in an unfolded configuration, the maximum longitudinal dimension of the secondary fastening component is disposed outboard of the longitudinal foldline and the inboard-most extent of the secondary fastening component is disposed inboard of the longitudinal foldline.

9. The absorbent article of claim 8, wherein the second portion comprises an opacity that is at least 15% greater than an opacity of the first portion.

10. The absorbent article of claim 8, wherein the first portion and second portion differ in color intensity.

11. The absorbent article of claim 8, wherein the secondary fastening component comprises a fastening component area and the first portion overlaps at least 20% of the fastening component area.

12. The absorbent article of claim 11, wherein the first portion overlaps at least 50% of the fastening component area.

13. The absorbent article of claim 8, wherein the first portion differs from the second portion by one of the following: color, color intensity, transparency, reflection, and saturation.

14. The absorbent article of claim 13, wherein the secondary fastening component is the same as a color of surrounding materials of the absorbent article.

15. The absorbent article of claim 14, wherein a color of the first portion of the graphic is different from a color of the second portion of the graphic.

16. The absorbent article of claim 8, wherein a portion of the secondary fastening component extends outside the graphic.

17. The absorbent article of claim 8, wherein the secondary fastening component is different from the graphic.

18. An absorbent article comprising: a first waist region, a second waist region, a crotch region disposed between the first and second waist regions; a topsheet, a backsheet, and an absorbent core disposed between the topsheet and backsheet; a longitudinal foldline disposed substantially parallel to a longitudinal axis of the absorbent article about which a portion of the first waist region and/or a portion of the second waist region is folded laterally back over itself when the absorbent article is in a folded configuration; and a primary fastening system and secondary fastening system, wherein the primary fastening system comprises a primary fastening component disposed in the second waist region and a primary receiving component disposed in the first waist region and operatively engageable with the primary fastening component, wherein the secondary fastening system comprises a secondary fastening component disposed in the first waist region and a secondary receiving component disposed in the second waist region and operatively engageable with the secondary fastening component, wherein the secondary fastening component comprises a maximum longitudinal dimension, wherein the maximum longitudinal dimension of the secondary fastening component is disposed outboard of an inboard-most extent of the secondary fastening component, and wherein in an unfolded configuration, the maximum longitudinal dimension of the secondary fastening component is disposed outboard of the longitudinal foldline and the inboard-most extent of the secondary fastening component is disposed inboard of the longitudinal foldline.

* * * * *